US006809205B1

(12) United States Patent
Elnagar et al.

(10) Patent No.: US 6,809,205 B1
(45) Date of Patent: Oct. 26, 2004

(54) PROCESS FOR PRODUCING N-HALOGENATED ORGANIC COMPOUNDS

(75) Inventors: Hassan Y. Elnagar, Baton Rouge, LA (US); Bruce C. Peters, Baton Rouge, LA (US); Edgar E. Spielman, Jr., Baton Rouge, LA (US); Dustin H. Thomas, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 09/484,844

(22) Filed: Jan. 18, 2000

(51) Int. Cl.$^7$ .................... C07D 233/74; C07D 233/82

(52) U.S. Cl. ................................ 548/320.5

(58) Field of Search ...................... 548/320.5

(56) References Cited

U.S. PATENT DOCUMENTS

| | | | |
|---|---|---|---|
| 2,130,805 A | 9/1938 | Levine ................ | 210/28 |
| 2,392,505 A | 1/1946 | Rogers ............... | 260/309.5 |
| 2,398,598 A | 4/1946 | Rogers ............... | 260/309.5 |
| 2,779,764 A | 1/1957 | Paterson ............. | 260/309.5 |
| 2,795,556 A | 6/1957 | Quinn ................ | 252/187 |
| 2,868,787 A | 1/1959 | Paterson ............. | 260/248 |
| 2,920,997 A | 1/1960 | Wolf et al. ........... | 167/33 |
| 2,971,959 A | 2/1961 | Waugh et al. ......... | 260/309.5 |
| 2,971,960 A | 2/1961 | Waugh et al. ......... | 260/309.5 |
| 3,121,715 A | 2/1964 | Waugh et al. ......... | 260/248 |
| 3,147,259 A | 9/1964 | Paterson ............. | 260/248 |
| 3,345,371 A | 10/1967 | Paterson ............. | 260/192 |
| 4,078,099 A | 3/1978 | Mazzola .............. | 427/213 |
| 4,126,717 A | 11/1978 | Mazzola .............. | 427/220 |
| 4,136,052 A | 1/1979 | Mazzola .............. | 252/94 |
| 4,242,216 A | 12/1980 | Daugherty et al. ..... | 252/103 |

(List continued on next page.)

FOREIGN PATENT DOCUMENTS

| | | |
|---|---|---|
| CA | 1230825 | 12/1987 |
| CA | 2042430 | 11/1991 |
| CA | 2163596 | 9/1996 |
| EP | 0177645 | 4/1986 |
| EP | 0206725 | 12/1986 |
| EP | 0228593 | 7/1987 |
| EP | 0581826 | 9/1995 |
| GB | 1054243 | 1/1967 |
| GB | 1600289 | 10/1981 |
| GB | 2273106 | 6/1994 |
| WO | 8910696 | 11/1989 |
| WO | 9630491 | 10/1996 |
| WO | 9715652 | 5/1997 |
| WO | 9720546 | 6/1997 |
| WO | 9720909 | 6/1997 |
| WO | 97-43264 | 11/1997 |
| WO | 9743392 | 11/1997 |
| WO | 0034186 | 6/2000 |

OTHER PUBLICATIONS

Corral et al., "Substitution in the Hydantoin Ring. III. Halogenation", J. Org. Chem., 1963, vol. 28, ppg. 1100–1104.
Jolles, "General Methods of Bromination", Bromine and its Compounds, 1966, Ernest Benn, London, ppg.. 365.
March, "Advanced Organic Chem.", 1992, $4^{th}$ Edition, ppg. 639–640.
Markish et al., "New Aspects on the Preparation of 1,3–Dibromo–5,5–Dimethylhydantoin", Ind. Eng. Chem. Res. 1995, vol. 34, ppg. 2125–2127.
Orazi, et al., "Halogenacion con 3–Bromo–5, 5–Dimetil–Hidantoina", Anales Assoc. Quim. Argentina, 1949, vol. 37, ppg. 192–196. (Not translated).
Orazi, et al., "Halogenacion Con 1–3–Dibromo–5, 5–Dimetil–Hidantoina", Anales Assoc. Quim. Argentina, 1950, vol. 38, ppg. 5–11. (Not translated).
Petterson, "N–Halogen Compounds I. Decomposition of 1,3–Dichloro–5,5–dimethylhydantoin in Water at pH 9", J. Org. Chem., 1959, vol. 24, ppg. 1414–1419.
Chowhan et al., "Hardness Increase Induced by Partial Moisture Loss in Compressed Tablets and Its Effect on In Vitro Dissolution", J. Pharm. Sciences, Oct. 1978, vol. 67, No. 10, ppg. 1385–1389.
Krycer et al., "An Evaluation of Tablet Binding Agents Part II. Pressure Binders", Powder Technology, 1983, vol. 34, ppg. 53–56.
HCAPLUS Abstract of JP 07171576 A2 issued 1995.
HCAPLUS Abstract of JP 07277912 A2 issued 1995.
HCAPLUS Abstract of JP 08027119 A2 issued 1996.
HCAPLUS Abstract of JP 08239699 A2 issued 1996.
HCAPLUS Abstract of JP 09087684 A2 issued 1997.
HCAPLUS Abstract of JP 09227317 A2 issued 1997.

Primary Examiner—Laura L. Stockton
(74) Attorney, Agent, or Firm—Edgar E. Spielman, Jr.

(57) ABSTRACT

The process enables highly effective N-halogenation of a compound having one or more halogenatable amido or imido functional groups in the molecule. The process involves, for example, concurrently feeding into a reactor (i) water, inorganic base, and the compound to be N-halogenated, e.g., a hydantoin, and a feed of (ii) a brominating agent and/or a chlorinating agent. The proportions of these feeds are such that the pH is kept within the range of ca. 5.5–8.5 (preferably 6.5–8.5, and most preferably 6.8–7.2) and one or more of the amido or imido nitrogen atoms is substituted by a bromine or chlorine atom. A feature of the process is that it can be conducted at elevated temperatures as high as about 90° C. without appreciable thermal decomposition of reactants or product. The resultant product continuously precipitates in high yield and purity. Moreover, products can be produced that are very pale yellow to almost pure white in appearance. Further, the process has been found capable of producing 1,3-dibromo-5,5-dimethylhydantoin with far larger particle sizes than previously produced on a commercial basis.

120 Claims, No Drawings

U.S. PATENT DOCUMENTS

| | | | |
|---|---|---|---|
| 4,327,151 A | 4/1982 | Mazzola | 428/407 |
| 4,427,692 A | 1/1984 | Girard | 424/273 R |
| 4,465,839 A | 8/1984 | Sculte et al. | 548/310 |
| 4,532,330 A | 7/1985 | Cole | 548/311 |
| 4,537,697 A | 8/1985 | Girard | 252/90 |
| 4,560,766 A | 12/1985 | Girard et al. | 548/311 |
| 4,571,333 A | 2/1986 | Hsiao et al. | 424/22 |
| 4,597,941 A | 7/1986 | Bottom et al. | 422/37 |
| 4,621,096 A | 11/1986 | Cole | 514/389 |
| 4,654,424 A | 3/1987 | Girard et al. | 548/311 |
| 4,677,130 A | 6/1987 | Puzig | 514/389 |
| 4,698,165 A | 10/1987 | Theyson | 210/755 |
| 4,713,079 A | 12/1987 | Chun et al. | 8/101 |
| 4,728,453 A | 3/1988 | Choy | 252/91 |
| 4,745,189 A | 5/1988 | Lee et al. | 544/221 |
| 4,803,079 A | 2/1989 | Hsiao et al. | 424/468 |
| 4,867,895 A | 9/1989 | Choy | 252/91 |
| 4,919,841 A | 4/1990 | Kamel et al. | 252/186.26 |
| 4,925,866 A | 5/1990 | Smith | 514/389 |
| 5,338,461 A | 8/1994 | Jones | 210/755 |
| 5,339,889 A | 8/1994 | Bigham | 165/1 |
| 5,422,126 A | 6/1995 | Howarth et al. | 424/723 |
| 5,565,109 A | 10/1996 | Sweeny | 210/755 |
| 5,565,576 A | 10/1996 | Hall et al. | 548/317.1 |
| 5,578,559 A | 11/1996 | Dolan et al. | 510/192 |
| 5,591,692 A | 1/1997 | Jones et al. | 504/124 |
| 5,603,941 A | 2/1997 | Farina et al. | 424/405 |
| 5,610,126 A | 3/1997 | Barford et al. | 510/191 |
| 5,614,528 A | 3/1997 | Jones et al. | 514/258 |
| 5,670,451 A | 9/1997 | Jones et al. | 504/134 |
| 5,750,061 A | 5/1998 | Farina et al. | 264/117 |
| 5,756,440 A | 5/1998 | Watanabe et al. | 510/191 |
| 5,763,376 A | 6/1998 | Ward et al. | 510/191 |
| 5,780,641 A | 7/1998 | Yerushalmi et al. | 548/320.5 |
| 5,859,060 A | 1/1999 | Platt | 514/569 |
| 5,942,153 A | 8/1999 | Heydel | 252/187.33 |
| 5,958,853 A | 9/1999 | Watanabe | 510/191 |
| 5,972,864 A | 10/1999 | Counts | 510/192 |
| 5,981,461 A | 11/1999 | Counts et al. | 510/365 |

PROCESS FOR PRODUCING N-HALOGENATED ORGANIC COMPOUNDS

REFERENCE TO OTHER APPLICATIONS

Commonly-owned copending Application Ser. No. 09/484,687, filed Jan. 18, 2000, by us and one of our colleagues, describes and claims 1,3-dibromo-5,5dimethylhydantoin particulate solids producible by the processes of this Application, such solids having unprecedented enhanced properties, and compacted articles made from such particulate solids without use of a binder. Commonly-owned copending Application Ser. No. 09/487,816, filed Jan. 18, 2000, by one of us and one of our colleagues, relates in part to converting 1,3-dihalo-5,5-dimethylhydantoins into compacted articles using novel binders. Commonly-owned copending Application Ser. No. 09/484,938, filed Jan. 18, 2000, by some of our colleagues, describes and claims methods for effecting efficacious microbiological control utilizing 1,3-dibromo-5,5-dimethylhydantoin in novel compacted or non-compacted forms. Commonly-owned copending Application Ser. No.09/484,891, filed Jan. 18,2000, by one of our colleagues relates to the compacting of 1,3dihalo-5,5-dimethylhydantoins other than 1,3-dibromo-5,5 dimethyl-hydantoin without use of binders, and to the novel compacted forms so produced. Commonly-owned copending Application SER. No.09/483,896, Jan. 18,2000, filed by one of us and one of our colleagues relates to the granulation of small average particle size 1,3-dibromo-5,5-dimethylhydantoin and also to the compaction of such granulated products to form larger-sized articles.

TECHNICAL FIELD

This invention relates to novel, highly efficient processes for the preparation of N-halogenated amides or imides such as N-halogenated hydantoins, succinamides, succinimides, phthatamides, phthalimides, cyanuric acid, glycolurils, and the like. Preferred aspects of this invention relate to novel, highly efficient processes for the preparation of 1,3-dihalo-5,5-dimethylhydantoins. As used herein, such terms as halogen, halogenated, and halo refer to bromine and/or chlorine.

BACKGROUND

Various N-halogenated amides and imides are of known utility as chemical intermediates, as halogenating agents in organic syntheses, and as biocidal agents. See for example, U.S. Pat. Nos. 2,868,787; 2,920,997; and 2,971,959.

1,3-Dihalo-5,5-dialkylhydantoins, especially 1,3-dibromo-5,5 limethylhydantoin, 1,3-dichloro-5,5-dimethylhydantoin, 1-bromo-3-chloro-5,5-dimethylhydantoin, and 1-chloro-3-bromo-5,5-dimethylhydantoin, or mixtures of two or more of them, are biocidal agents for use in water treatment. These compounds are, in general, sparingly soluble in water. Each of these compounds except 1,3-dibromo-5,5-dimethylhydantoin, has been supplied in compacted solid forms such as granules, tablets, or briquettes, and delivered into the water being treated by means of water flow through an erosion feeder. So far as is known, 1,3-dibromo-5,5-dimethylhydantoin powder has not been converted into a compacted form for such use.

Over the years considerable effort has been devoted to the search for improved methods for producing N-halogenated amides or imides. In U.S. Pat. No. 2,971,960 N-brominated compounds such as N-brominated 5,5-di-lower-alkyl hydantoins are formed by treating the alkylhydantoin with bromine in an acidic aqueous solution containing hypochlorite, preferably at a pH between 1 and 4. However, the method of choice has been halogenation of the alkylhydantoin in a basic aqueous medium. Almost invariably the halogen has been introduced into, or formed in situ in, the aqueous medium containing the alkylhydantoin. See in this connection U.S. Pat. Nos. 2,398,598; 2,779,764; 2,868,787; 2,920,997; 2,971,959; 3,121,715; 3,147,259; 4,532,330; 4,560,766; 4,654,424; 4,677,130; 4,745,189; WO 97/43264, published 20 Nov. 1997; Orazi and Meseri, *Anales Assoc. Quim. Argentina*, 1949,37, 192–196; Orazi and Meseri, *Anales Assoc. Quim. Argentina*, 1950, 38, 5–11; Corral and Orazi, *J. Org. Chem.*, 1963, 23, 1100–1104; Jolles, *Bromine and its Compounds*, Ernest Benn, London, 1966, p. 365; and Markish and Arrad, *Ind. Eng. Chem. Res.*, 1995, 34, 2125–2127.

Shortcomings of prior processes for the N-halogenation of amides and imides include the requirement for careful temperature control (particularly in order to avoid sudden exotherms), long reaction times, foaming due to evolution of gases from decomposition of reactants and/or reaction products, and products of inconsistent quality.

In the case of 1,3-dihalo-5,5-dimethylhydantoins, the provision of a process capable of producing the product as relatively large particles is a desirable objective. U.S. Pat. No. 4,745,189 refers to formation of N,N'-bromochloro-5,5-dimethylhydantoin products comprising relatively large particles. Unfortunately, however, the process requires halogenation of dimethylhydantoin in an aqueous mixture under alkaline conditions in the presence of a halogenated alicyclic organic compound such as dichloromethane.

It would be of considerable advantage if a new way could be found of producing N-halogenated amides or imides while avoiding or at least minimizing the extent of the shortcomings referred to above. It would also be of great advantage if a way could be found of producing 1,3-dihalo-5,5-dimethylhydantoins having larger average particle size than produced by methods known heretofore. Also it would be of considerable advantage if the production of a larger average particle size product could be accomplished without need for use of a halogenated organic solvent in the reaction mixture.

This invention is deemed to fulfill these objectives in a most effective and efficient manner.

SUMMARY OF THE INVENTION

In accordance with this invention processes are provided which are characterized by high efficiency, uniform product consistency, good product color, and efficient utilization of reactants. In addition, this invention makes possible the conduct of exothermic N-halogenation reactions without use of costly refrigeration. Moreover, the processes of this invention can be run in a batch mode, in a semi-batch mode, or in a continuous mode, and in any such mode it is possible, when producing products devoid of chromophoric groups, to obtain high yields of very pale yellow to almost pure white products. And no haloorganic solvent or co-solvent of any kind is required in the processes of this invention.

Furthermore, this invention makes possible the production of 1,3dihalo-5,5-dimethylhydantoins with large average particle sizes without use of any halogenated solvent or co-solvent in the process. For example, 1,3-dibromo-5,5-dimethylhydantoin with an average particle size of at least 175 microns can now be readily formed pursuant to this invention. In fact, 1,3-dibromo-5,5-dimethylhydantoin, with an average particle size of over 300 microns has been produced using a process of this invention. As will be seen hereinafter, measurements carried out on samples of several commercially-available 1,3-dibromo-5,5-dimethylhydantoins obtained from different commercial sources showed that the largest average particle size of these commercial products was only about 162 microns.

One of the embodiments of this invention is a process for the N-halogenation of a compound having in the molecule at least one halogenatable amido or imido nitrogen atom. The process comprises concurrently, or substantially concurrently, feeding (a) a compound having in the molecule at least one N-halogenatable amido or imido nitrogen atom, (b) an inorganic base, (c) a brominating agent and/or a chlorinating agent, and (d) water, where (a), (b), (c), and (d) are fed individually and/or in any combination(s) whereby the feeds come together in a reaction zone. In addition, (a), (b), (c), and (d) are fed in proportions such that at least one such amido or imido nitrogen atom is substituted by a bromine or chlorine atom, thereby forming product which precipitates in an aqueous reaction mixture, and such that the pH of the aqueous reaction mixture is continuously or substantially continuously maintained in the range of about 5.5 to about 8.5 during all or substantially all of the time such feeding is occurring.

Another embodiment involving the N-halogenation of a compound having in the molecule at least one halogenatable amido or imido functional group is a another concurrent feeding process. In this case, there are at least two separate but concurrent or substantially concurrent feeds to a reactor. One such feed is a brominating agent or a chlorinating agent. One or more other separate feeds deliver to the reactor a compound having in the molecule at least one N-halogenatable amido or imido nitrogen atom, an inorganic base, and water. A preferred process of this embodiment comprises concurrently feeding into in a reaction zone:

A) separate feeds of (i) an aqueous solution or slurry formed from an inorganic base and a compound having in the molecule at least one halogenatable amido or imido nitrogen atom, and (ii) a brominating agent and/or a chlorinating agent; or B) at least three separate feeds, one of which is a brominating agent and/or a chlorinating agent, and at least two other feeds, at least one of which is selected from (a) and (b); and at least one of which is selected from (c) and (d), wherein
  (a) is an aqueous solution or slurry formed from an inorganic base,
  (b) is an aqueous solution or slurry formed from an inorganic base and a compound having in the molecule at least one halogenatable amido or imido nitrogen atom,
  (c) is a compound having in the molecule at least one halogenatable amido or imido nitrogen atom, and
  (d) is an aqueous solution or slurry formed from a compound having in the
    molecule at least one halogenatable amido or imido nitrogen atom;
in proportions such that at least one such amido or imido nitrogen atom is substituted by a bromine or chlorine atom, thereby continuously or substantially continuously forming product which precipitates in an aqueous reaction mixture continuously or substantially continuously, during all or substantially all of the time the concurrent feeding is occurring, and such that the pH of the mixture is continuously or substantially continuously maintained in the range of about 5.5 to about 8.5 during all or substantially all of the time the concurrent feeding is occurring.

Another preferred process for the N-halogenation of a compound having at least one halogenatable amido or imido functional group in the molecule is one in which there are in essence two separate feeds to effect the desired reaction. Such process comprises concurrently feeding separate feeds into a reaction zone so that the feeds form, or continue to form, a reaction mixture. These separate feeds are composed of (i) an aqueous solution or slurry formed from an inorganic base and a compound having in the molecule at least one halogenatable amido or imido nitrogen atom, and (ii) a brominating agent and/or chlorinating agent in proportions such that at least one such amido or imido nitrogen atom is substituted by a bromine or chlorine atom and the resultant product precipitates continuously or substantially continuously in an aqueous reaction mixture during all or substantially all of the time the concurrent feeding is occurring, and such that the pH of the mixture is continuously or substantially continuously maintained in the range of about 6.5 to about 8.5.

A particularly preferred group of reactants used in the practice of this invention is comprised of the 5-hydrocarbyl and especially the 5,5-dihydrocarbyl hydantoins. Of these reactants the 5,5-dialkylhydantoins are even more preferred. Accordingly, still another preferred embodiment of this invention is a process for the production of a 1,3-dihalo-5,5-dimethylhydantoin, which process comprises concurrently feeding into contact with each other feed streams of (i) water, inorganic base, and 5,5-dimethyihydantoin, these being fed separately and/or in any combination(s), and (ii) a separate feed of abrominating agent and/or a chlorinating agent, in proportions such that 1,3-dihalo-5,5-dimethylhydantoin is formed in an aqueous reaction mixture in which the pH of such mixture is continuously or substantially continuously maintained in the range of about 6.5 to about 8.5, and where the 1,3dihalo-5,5-dimethylhydantoin precipitates during all or substantially all of the time the concurrent feeding is occurring.

Another preferred process of this invention is a process in which the N-halogenation is conducted on a semi-batch or more preferably on a continuous basis. Such process comprises:

I) concurrently and continuously feeding into a reactor containing an aqueous reaction mixture:
  A) separate feeds of (i) an aqueous solution or slurry formed from an inorganic base and a compound having in the molecule at least one halogenatable amido or imido nitrogen atom, and (ii) a brominating agent and/or a chlorinating agent; or
  B) at least three separate feeds, one of which is a brominating agent and/or a chlorinating agent, and at least two other feeds, at least one of which is selected from (a) and (b); and at least one of which is selected from (c) and (d), wherein
    (a) is an aqueous solution or slurry formed from an inorganic base,
    (b) is an aqueous solution or slurry formed from an inorganic base and a compound having in the molecule at least one halogenatable amido or imido nitrogen atom,
    (c) is a compound having in the molecule at least one halogenatable amido or imido nitrogen atom, and
    (d) is an aqueous solution or slurry formed from a compound having in the molecule at least one halogenatable amido or imido nitrogen atom;

in proportions such that at least one such amido or imido nitrogen atom is substituted by a bromine or chlorine atom and a precipitate of the resultant product precipitates in an aqueous reaction mixture during all or substantially all of the time the concurrent feeding is occurring, and such that the pH of the reaction mixture is continuously or substantially continuously maintained in the range of about 5.5 to about 8.5; and II) periodically or continuously removing precipitate and a portion of the reaction mixture from the reactor.

When using a brominating agent in any of the above processes, it is possible pursuant to this invention to recover the bromine values produced as bromide in the process. Such an operation can improve the overall process economics. One such embodiment of the invention comprises:

a) concurrently feeding into a reactor (i) water, inorganic base, and a compound having in the molecule at least one halogenatable amido or imido nitrogen atom, these components being fed separately and/or in any combination(s), and (ii) a separate feed of a brominating agent, in proportions such that (iii) at least one such amido or imido nitrogen atom is substituted by a bromine atom, (iv) the product continuously or substantially continuously precipitates in an aqueous reaction mixture in which the pH is continuously or substantially continuously maintained in the range of about 5.5 to about 8.5, and (v) an aqueous solution of co-product inorganic bromide salt is formed;

b) separating precipitate from the aqueous solution; and c) oxidizing co-product inorganic bromide salt in the solution to form elemental bromine.

Preferably the pH in each of the above embodiments is maintained in the range of about 6.5 to about 8.5. It is particularly preferred to conduct the above processes while maintaining the pH within the range of about 6.8 to about 7.2, especially when the N-halogenatable reactant is a hydantoin.

As noted above, each process of this invention can be conducted in a batch mode, in a semi-batch mode, or in a continuous mode.

Other embodiments and features of the invention will become still further apparent from the ensuing description and appended claims.

FURTHER DETAILED DESCRIPTION

This invention is applicable to the N-halogenation of a wide variety of compounds having at least one halogenatable amido or imido nitrogen atom in the molecule. Thus, the compound may contain only a single halogenatable functionality or it may contain a plurality of such halogenatable functional groups. Moreover, the compound may contain both halogenatable amido functionality and halogenatable imido functionality in the molecule. Among typical N-halogenatable compounds that can be utilized in the process of this invention are such compound types as hydantoins, succinamides, succinimides, phthalimides, phthalimides, cyanuric acid, glycolurils, oxazolidinones, sulfonamides, barbiturates, imidazolinones, ureas, oxazoles, and the like. For ease of reference such compounds are sometimes referred to hereinafter as N-halogenatable compounds.

Throughout this disclosure the term "N-halogenatable" with reference to reactions involving amido groups (where the nitrogen atom can have two hydrogen atoms as substituents thereon), refers to removal from the nitrogen atom of either one hydrogen atom or both hydrogen atoms being subjected to deprotonation and halogenation, unless the context expressly indicates that only one of such hydrogen atoms is to be removed or that both such hydrogen atoms are to be removed.

In most cases the processes of this invention will be applied to the N-halogenation of N-halogenatable amides, especially cyclic amides, or to the N-halogenation of N-halogenatable imides, especially cyclic imides. However, of the N-halogenatable compounds, the hydantoins are preferred. More preferred are 5-hydrocarbyl and 5,5-dihydrocarbyl hydantoins. Particularly preferred hydantoins are the 5-alkyl and 5,5-dialkyl hydantoins, especially those in which each alkyl group contains up to about 6 carbon atoms. Still more preferred are 5,5-dialkyl hydantoins in which each alkyl group contains, independently, up to 3 carbon atoms. Most especially preferred is 5,5-dimethylhydantoin.

A wide variety of inorganic bases are suitable for use in the process of this invention. Typically these are water-soluble basic salts or oxides of an alkali metal or an alkaline earth metal. Preferred bases include sodium oxide, sodium hydroxide, sodium carbonate, sodium bicarbonate, potassium oxide, potassium hydroxide, potassium carbonate, potassium bicarbonate, calcium oxide, calcium hydroxide, or a mixture of any two or more of them.

Reactions pursuant to this invention can be carried out with various proportions of water, inorganic base, and N-halogenatable compound. When the inorganic base has a monovalent cation, the feeds should be controlled and maintained such that per liter of water being fed, there are from about 0.5 to about 2.5 moles of halogenatable amido and/or imido nitrogen atoms to be deprotonated and from about 0.5 to about 2.5 moles of the base. On the other hand, when the inorganic base has a divalent cation, the feeds should be controlled and maintained such that per liter of water being fed, there are about 0.5 to about 2.5 moles of halogenatable amido and/or imido nitrogen atoms to be deprotonated, and from about 0.25 to about 1.25 moles of the base.

In preferred embodiments the proportions among water, inorganic base, and N-halogenatable compound being fed are as follows:

A) where the inorganic base has a monovalent cation, there are per liter of water, from about 1.0 to about 1.5 moles of halogenatable amido and/or imido nitrogen atoms and from about 1.0 to about 1.5 moles of the base; and B) where the base has a divalent cation, there are per liter of water, about 1.0 to about 1.5 moles of halogenatable amido and/or imido nitrogen atoms and from about 0.5 to about 0.75 moles of the base.

When conducting the preferred embodiments of this invention involving use of a 5,5-dialkylhydantoin, particularly 5,5-dimethylhydantoin, the proportions of water, inorganic base, and 5,5-dimethylhydantoin being fed should be such that when using an inorganic base having a monovalent cation, there can be from about 0.5 to about 2.5 moles of 5,5-dimethylhydantoin and from about 1.0 to about 5.0 moles of the base, per liter of water being fed, and preferably from about 1.0 to about 1.5 moles of 5,5-dimethylhydantoin and from about 2.0 to about 3.0 moles of the base, per liter of water being fed. When using an inorganic base having a divalent cation, there can be from about 0.5 to about 2.5 moles of 5,5-dimethylhydantoin and from about 0.5 to about 2.5 moles of the base, per liter of water being fed, and preferably about 1.0 to about 1.5 moles of 5,5-dimethylhydantoin and from about 1.0 to about 1.5 moles of the base, per liter of water being fed.

In order to achieve the best results, the amount of base used is the stoichiometric quantity, or is substantially the stoichiometric quantity, theoretically required to deprotonate the nitrogen atom of at least one imido group of the N-halogenatable compounds, or to fully or partially deprotonate the nitrogen atom of at least one amido group of such compounds. Thus, if the N-halogenatable compound has but one halogenatable imido group in the molecule (and no halogenatable amido group), the amount of the base used will be sufficient to fully deprotonate the nitrogen atom of that imido group. Similarly, in the case of an N-halogenatable compound having 2 or more halogenatable imido groups in the molecule the amount of base used will be sufficient to deprotonate as many of the nitrogen atoms of such imido groups as is desired. In the case of an N-halogenatable compound having a single halogenatable amido group in the molecule (i.e., a group of the formula —CO—NH$_2$), the amount of the base used can either be the amount sufficient to partially deprotonate such nitrogen atom (whereby monohalogenation is achieved on the nitrogen atom) or to fully deprotonate such nitrogen atom (whereby dihalogenation is achieved on the nitrogen atom). With N-halogenatable compounds having two or more halogenatable amido groups in the molecule, the amount of the base used can be such as to deprotonate to the desired extent one or more of such amido nitrogen atoms. When the N-halogenatable compound contains at least one halogenatable amido group and at least one halogenatable imido group (e.g., as in the case of a hydantoin), it is possible to selectively deprotonate the nitrogen atom of the imido group without significantly affecting the amido group. This is accomplished by employing an amount of the base stoichiometrically required to deprotonate the nitrogen atom of the imido group (i.e., the functional group having the greater acidity). Alternatively, it is possible to deprotonate the nitrogen atom of the imido group and the nitrogen atom of the amido group by use of an amount of base sufficient to deprotonate the nitrogen atoms of both such groups.

The water, inorganic base, and the N-halogenatable compound can be fed individually or in any combination or mixture. However, it is advantageous to feed the inorganic base as an aqueous solution either with or without the co-presence of the N-halogenatable compound. In this way, the heat generation that occurs when dissolving a base in water takes place prior to the introduction of such solution of aqueous base into the reaction zone. Most preferably, an aqueous solution of the inorganic base is formed, and to this solution is added the N-halogenatable compound. Such a procedure not only safeguards against excessive heat generation which might otherwise adversely affect the N-halogenatable compound, but simplifies the feeding operation and control of the proportions being fed. For best results, it is desirable to employ feed solutions having in the range of about 0.5 to about 2.5 moles of the N-halogenatable compound per liter of water. In forming such solutions, use of aqueous alkaline solutions in the range of about 0.5 to about 5.0 moles of base per liter of water is preferred.

In the practice of this invention, halogenation of the N-halogenatable compound is accomplished by use of a brominating agent and/or a chlorinating agent. Thus use can be made of bromine, chlorine, bromine chloride, bromine and chlorine, a bromide salt and chlorine and/or a source of hypochlorite anion, or an organic brominating or organic chlorinating agent such as N-bromosuccinimide, N-chlorosuccinimide, or pyridinium tribromide, and the like. Of these halogenating agents, bromine, chlorine, bromine chloride, bromine and chlorine, a bromide salt and chlorine and/or a source of hypochlorite anion are preferred. Particularly preferred are bromine and mixtures of bromine and chlorine (which will include or consist of bromine chloride). Without desiring to be bound by theoretical considerations, it is believed that the actual species which carry out the halogenation in the aqueous reaction mixture can include, for example, one or more of $Br_2$, $Cl_2$, $BrCl$, $OBr^{\ominus}$, $OCl^{\ominus}$, $Br_3^{\ominus}$, $BrCl_2^{\ominus}$, $Cl_3^{\ominus}$, $Cl^{\oplus}$, and $Br^{\oplus}$. Whatever the actual halogenating species may be, the important thing is to feed to the aqueous reaction mixture a suitable halogenating agent that results in N-halogenation of at least one nitrogen atom of an amido or imido group of the compound being halogenated.

If both bromine and chlorine are used, they can be fed as separate feeds. Alternatively, they can be premixed in any desired proportions whereby the mixture being fed will contain bromine chloride, and if mixed in molar proportions other than 1:1, will also contain the halogen used in excess. In lieu of chlorine, an alkali or alkaline earth metal hypochlorite can be used as the chlorine source. Typically the hypochlorite salt will be fed in the form of an aqueous solution or slurry. However, it is also possible to feed a solid hypochlorite salt such as calcium hypochlorite directly into the aqueous reaction mixture. When bromination is desired, the feed can be an alkali metal bromide or an alkaline earth metal bromide, and a source of chlorine, such as chlorine or an aqueous solution or slurry of an alkali or alkaline earth metal hypochlorite, such as sodium hypochlorite solution, in amounts sufficient to generate bromine in situ. It is also possible to feed a solid hypochlorite salt such as calcium hypochlorite to the aqueous reaction mixture in order to generate the bromine in situ. Usually feeds of this type will result in formation of products containing both bromine and chlorine in the molecule. While in principle other sources of bromine or chlorine may be used, such as organic compounds containing loosely bound bromine or chlorine, the use of such organic halogenating agents is not preferred as their use can complicate product workup and recovery operations. Moreover, such organic halogenating agents tend to be more expensive than such sources as bromine or chlorine, or sodium bromide and chlorine.

The bromine or chlorine should be fed subsurface to the aqueous phase in the reaction zone so as to ensure intimate contact with the N-halogenatable compound being used. When using an alkali metal bromide or an alkaline earth metal bromide and chlorine to generate bromine in situ, the bromide salt can be fed as a separate feed, typically as a water solution, or it can be fed along with an aqueous solution or slurry formed from the water-soluble base and the N-halogenatable compound. In any such case, the chlorine used therewith should be fed subsurface to the aqueous phase in the reaction zone.

Chlorine will typically be fed into the reaction mixture as a liquid, but can be fed in the vapor state, if desired. Bromine can be fed into the reaction mixture either as a gas or as a liquid. Preferably the bromine is fed in the vapor state subsurface to the liquid phase of the aqueous reaction mixture, and it is desirable to so feed the gaseous bromine in admixture with an inert gas such as nitrogen or argon.

Although it is desirable and preferred to feed diatomic halogens ($Cl_2$, $Br_2$, $BrCl$, or mixtures thereof, and where the $Cl_2$ itself is being used as the chlorinating agent or is being used in combination with a bromine source such as an alkali metal bromide and/or an alkaline earth bromide) subsurface to the liquid phase of the aqueous reaction mixture, other ways of accomplishing the feeding can be used. One other way is to feed vaporous diatomic halogen into a headspace of a reactor while spraying aqueous reaction mixture and/or spraying or misting water into intimate contact with such vapors within the reactor. Other ways of establishing intimate contact of the diatomic halogen with the remainder of the components from which the aqueous reaction mixtures is formed include feeding the halogen as a liquid and/or as a solution into the aqueous reaction mixture, and in such case the halogen can be fed above the surface of the aqueous reaction mixture, if desired. In short, this invention contemplates the feeding of the halogen in any conceivable way that accomplishes the objective of bringing the components into intimate contact with each other so that the intended N-halogenation reaction will occur. In all cases, agitation of the aqueous reaction mixture is advantageous.

It is to be noted that when the term "subsurface" is used anywhere in this document, including the claims, the term does not denote that there must be a headspace in the reaction zone. For example, if the reaction zone is completely filled with the aqueous reaction mixture (with equal rates of incoming and outgoing flows), the term "subsurface" means in this case that the substance being fed subsurface is being fed directly into the body of the aqueous reaction mixture, the surface thereof being defined by the enclosing walls of the reaction zone.

In this connection, in one of the embodiments of this invention, the N-halogenatable compound, inorganic base, brominating agent and/or chlorinating agent, and water can be fed either individually and/or in any combination(s) including a combination of all such components. If all such components are fed in combination with each other, this can result in these components coming together outside of a typical reactor or reaction vessel. In practicing such feeding, the components can initially be brought into contact with each other in a mixing device in proximity to, but apart from, such reactor or reaction vessel. Suitable mixing devices include a static mixer, a conduit (preferably a conduit in which there is turbulent flow), or a jet mixer that produces a high velocity effluent stream. In all such cases, the mixing device itself in which all of the foregoing components first come into contact with each other is part of the reaction zone.

The processes of this invention can be conducted in any of a variety of modes of operation. For example, the processes can be carried out in a batch mode, in a semi-batch mode with constant overflow, in a semi-batch mode without overflow, or in a continuous mode. The engineering details concerning such modes of process operation are well known in the art, as witness, for example, *Perry's Chemical Engineer's Handbook*, 4th Edition, McGraw-Hill, copyright 1963.

In a continuous operation, usually and preferably, the effluent from the mixing device in which all of the foregoing components are first brought together is fed into a larger volume reactor or reaction vessel containing a body of the aqueous reaction mixture. Since reaction will begin essentially as soon as the foregoing components come into contact with each other, reaction will usually commence in such mixing device and will continue in the aqueous reaction mixture in the reactor or reaction vessel, which of course is also part of the reaction zone. Thus, it is desirable to place the mixing device, when using a mixing device, in close proximity to the larger volume reactor or reaction vessel and to move the components rapidly into, through, and from the mixing device and into a larger volume of aqueous reaction mixture in the larger reactor or reaction vessel. In this way, the time between initial contact among all of the components and the time when the aqueous reaction mixture comes into contact with a larger volume of the aqueous reaction mixture is kept short enough so that the temperature of the reaction mixture at any stage of the operation does not exceed about 90° C., and preferably does not exceed about 70° C. If desired, the mixing device, if used, can be cooled by indirect heat exchange with a cooling or refrigerated fluid.

When using a conduit with turbulent flow therein as the mixing device, such conduit can itself constitute the entire reactor or reaction vessel in a continuous operation. In other words, the reactor or reaction vessel itself can be a tubular reactor of sufficient length and volume for the reaction and precipitate formation to occur therein.

Preferably, the reactants are concurrently fed into a reaction zone composed of at least one reactor in which all of the components—whether fed individually or in any subcombination(s)—all come together for the first time and in which the N-halogenation reaction is initiated and carried out.

Preferably the concurrent feeds in the processes of this invention are continuous feeds. It is also preferable that the feeds are co-feeds—i.e., two feeds are utilized, namely (i) an aqueous solution or slurry formed from an inorganic base and a compound having in the molecule at least one halogenatable amido or imido nitrogen atom, and (ii) a brominating agent and/or chlorinating agent. However, it is also within the scope of this invention to conduct a tri-feed or other multi-feed process. Indeed, it is possible to utilize, for example, both a co-feed and a tri-feed although such an operation offers no particular advantage. In all cases, the feeds are proportioned such that at least one amido or imido nitrogen atom in the molecule is substituted by a bromine or chlorine atom. Product formation occurs almost immediately upon the reaction components coming in contact with each other, and if no solids-containing heel or solids-free mother liquor from a prior reaction is used, precipitation begins shortly thereafter. Once precipitation has commenced, product formation and precipitation occur continuously or substantially continuously during the concurrent feeds. When a solids-containing heel or solids-free mother liquor from a prior reaction is used; the precipitation begins almost immediately and continues to occur continuously or substantially continuously during the concurrent feeds. The feeds are proportioned such that the pH in the aqueous reaction mixture is maintained or substantially continuously maintained in the range of about 5.5 to about 8.5, preferably in the range of about 6.5 to about 8.5, and most preferably in the range of about 6.8 to about 7.2. In conducting the process, the materials in the concurrent feeds should rapidly come into intimate contact with each other. Thus, it is preferred to introduce the separate, but concurrent feeds, in close or relatively close proximity to each other and to provide sufficient agitation to cause such rapid intimate contact and resultant interaction among the components being fed.

In conducting the processes of this invention, observations to date indicate that the reaction and precipitate formation are extremely fast. When no solids-containing heel or solids-free mother liquor from a prior reaction is used, the slight delay in the commencement of precipitate formation at the beginning of the concurrent feeds is believed to be simply the time required for the aqueous reaction mixture to become suitably saturated with the product. When a solids-containing heel or solids-free mother liquor from a prior reaction is used, little or no delay occurs in the commencement of precipitate formation at the beginning of the concurrent feeds. Because the rapidity of the reaction, upon termination of the concurrent feeds, precipitation may continue to occur in the aqueous reaction mixture for only a very short period of time.

The use of the term "concurrent" does not exclude the possibility of inconsequential interruptions taking place during the feeds. Nor does this term imply that the feeds must start at exactly the same moment in time. In the case of a co-feed process, the two feeds can be initiated with an interval of time between such initiation as long as the interval is sufficiently short as to cause no material adverse effect upon the overall process. Likewise in the case of a tri-feed or multi-feed operation, there may be one or two different time intervals between or among the respective feeds, again provided that the time intervals are of sufficiently short duration to cause no material adverse effect upon the overall process.

The processes of this invention, whether performed in a batch mode, semi-batch mode, or continuous mode, are preferably conducted so that such things as the feeds, reaction, precipitate formation, and maintenance of specified pH occur "continuously" during the reaction. However, it cannot be stressed strongly enough that one must not gain the impression that inconsequential interruption in one or more of such things cannot occur. Interruptions which do not materially affect the conduct of the process are not excluded from the scope of this invention. To safeguard against hypertechnical legalistic word interpretation, it has been deemed prudent to employ terms such as "substantially continuously" in describing this invention. But whatever the terms used, the process should be conducted as one of ordinary skill in the art would carry out the processes after a thorough, unbiased reading of this entire disclosure and in keeping with the spirit of the invention gained from such a reading.

When conducted in a batch mode or when initiating a semi-batch or continuous process, it is preferred, although not required, to initially charge to the empty reactor either a solids-containing heel of a reaction mixture from a prior reaction in which the product to be formed had been formed or a solids-free mother liquor from such a prior reaction. Such heel or mother liquor typically has a pH in the range of about 6 to about 7, and usually contains up to 2 wt % of the product and/or a precursor thereof. Then the concurrent, suitably-proportioned feeds are initiated, typically at room temperature, and precipitate formation commences almost immediately, and in any event within a few minutes. In a batch operation, the feeds are typically continued until the reactor has been, or until the reactors have been, filled to the desired level. Usually at this point, the feeds are terminated, and the N-halogenated product which has formed and precipitated is recovered, typically by filtration, centrifugation, or decantation. Since the reaction is exothermic and rapid, long ride periods at the end of the feeding are normally unnecessary.

When operating in a continuous mode and once the continuous feeds have been initiated, the feeds may be adjusted in fine tuning the operation so as to establish and maintain the desired operating conditions for the steady-state operation. Such operation typically can be conducted without mishap for long periods of time before shutdown, e.g., for plant maintenance.

It can be seen therefore, whether operating in a batch mode, a semi-batch mode, or in a continuous mode, the initiation of the reaction with the utilization of a heel or mother liquor enables the more rapid achievement of efficient, steady-state operation than if a heel or mother liquor is not employed.

When feeding the brominating agent and/or chlorinating agent into the reactor, best results are achieved when such halogen source is introduced directly into the body of liquid within the reactor, i.e., below the surface of the heel or mother liquor when starting up the reaction and below the surface of the aqueous reaction mixture once the reaction has commenced. This will minimize the possibility of some of the halogen remaining in the headspace in the reactor and thus not participating in the reaction. Also feeds subsurface to the liquid phase of the reactor contents avoid splattering which can occur when, for example, liquid bromine strikes the surface of an aqueous mixture.

In a batch operation the aqueous reaction mixture is largely created and increased in volume by the feeds. In operations conducted in the batch, semi-batch, or continuous mode, it is highly desirable to vigorously agitate the reaction mixture to ensure thorough mixing of the reaction components.

Because of the short reaction and precipitation times which are features of processes of this invention, it is possible, indeed preferred, to conduct the processes in a semi-batch mode, and more preferably in a continuous mode. This in itself is a rarity, as the literature on N-halogenation of amides or imides is replete with teachings involving only batch operations. In the continuous mode, reactor size can be substantially reduced without a loss in product output.

If the reaction is performed in a reactor of sufficient size, the volume of the reactor contents can be cycled between predetermined low and high volumes with initiation of rapid draining when the volume reaches the high volume of reactor contents, and with discontinued draining once the volume reaches the low volume of reactor contents. However, it is preferred to conduct the process so that the volume of the contents of the reactor and the volume of the precipitate and portion of the reaction mixture removed from the reactor are equal or substantially equal whereby the volume of reactor contents remains constant or substantially constant. In this way, reactors with smaller volumes can be employed.

Thus, once steady-state conditions have been achieved in a continuous reactor, the separate feeds can be fed in appropriate proportions on a continuous basis, and the reactor contents maintained under the appropriate reaction conditions for virtually unlimited periods of time. Concurrently, a portion of the reaction mixture including precipitate (which mixture typically is in the form of a slurry) is being removed, usually and preferably continuously, from the reaction mixture so that the volume of the contents of the reactor remains more or less constant.

Another feature of this invention is that the co-product is a relatively pure aqueous saline solution, thus minimizing environmental and disposal problems. Moreover, when to using bromine as the halogen and an alkali or alkaline earth metal salt or oxide as the base in the process, the resultant co-product is an aqueous solution of alkali or alkaline earth metal bromide from which bromine can be recovered by oxidation of bromide ion to elemental bromine, for example by treatment of the solution with chlorine.

In typical, properly conducted batch operations, during at least about 80% of the period of time the separate feeds are being fed concurrently, and preferably during at least about 90% of the foregoing period of time, precipitate is being formed that typically is essentially pure product (e.g., with a purity of at least about 97%, and often as much as 99.9% purity). Also, typically the desired product is formed in a yield of at least about 80%, and often as high as 94% or more, based on the amount of the compound having at least one halogenatable amido or imido nitrogen atom used in the reaction. In typical, properly conducted continuous operations, once steady-state operation has been achieved, precipitate is continuously being formed that (a) also typically has a purity of at least about 96%, and often as much as 99.9%, and (b) typically is formed in a substantially continuous yield of at least about 85% based on the amount of the compound having at least one halogenatable amido or imido nitrogen atom being fed as a reactant in the process.

When properly conducted, the processes of this invention can produce 1,3-dihalo-5,5-dimethylhydantoins with an average particle size of at least about 200 microns, and often significantly larger than this.

If bromine is to be generated in situ, this is best accomplished by reaction between a suitable oxidant, preferably chlorine, and a bromine source such as a water-soluble alkali or alkaline earth metal bromide.

The processes of this invention can be carried out in various ways, such as in a batch mode, in a semi-batch mode, or, preferably, in a continuous mode. When conducting a continuous operation, it is desirable to design the operation such that the average residence time falls within the range of about 15 to about 100 minutes, and preferably in the range of about 30 to about 60 minutes. As with all of the numerical ranges given herein, departures therefrom are permissible whenever deemed necessary or desirable, provided only that such departures do not materially detract from the efficacy and effectiveness of the process.

An important feature of this invention is the concurrent feeding of the separate feeds referred to above. It is again to be emphasized that the term "concurrent" does not imply that the feeds must start at exactly the same time or that they must stop at exactly the same period of time. Rather, the term is used in the sense that during substantially the entire reaction period, the designated feeds are being maintained. It should also be understood that while these concurrent feeds are preferably continuous concurrent feeds, slight interruptions in a feed are acceptable provided that the duration of the interruption is sufficiently small as to cause no material disruption in the reaction. Thus as used herein, the terms "concurrent" and "continuous" should be understood to embrace the minor departures just referred to. Naturally, those skilled in the art will strive to utilize the concurrent feeds with as little nonconcurrence as possible. Likewise, those skilled in the art will of course seek to maintain the continuous feeds with as few interruptions as possible under the given circumstances in which the operation is being conducted. However, because the reaction mixtures are generally capable of standing for days without material change in composition, it is possible to interrupt an uncompleted operation (whether conducted in a batch mode, in a semi-batch mode, or in a continuous mode) for long periods of time should this become necessary.

Another highly important feature of this invention is the maintenance of the correct pH in the aqueous reaction mixture throughout substantially the entire reaction period. Here again, it is possible for slight departures to occur in the pH, particularly at the outset of the reaction. Such departures are within the ambit of this invention provided of course that no material adverse effects are encountered as a result of such departures. As noted above, the processes of this invention are typically conducted at a pH within the range of about 5.5 to about 8.5, and preferably in the range of about 6.5 to about 8.5. However, for best results the pH is most preferably maintained within the range of about 6.8 to about 7.2.

To maintain the desired pH in the aqueous reaction mixture, the rates at which the feeds of the base and the halogenating agent play an important role. In particular, the halogen should be fed or generated in situ at a rate insufficient to depress the pH below the desired level (e.g., 5.5, or preferably 6.5, or most preferably 6.8). In other words, the feed of halogen or the generation of halogen in situ should not be such as to decrease the pH (increase the acidity) of the reaction mixture to a pH significantly below about 5.5 for any substantial period of time. Likewise, the base, whether fed singly, as an aqueous solution of base, or in admixture with water and the N-halogenatable compound, should be fed at a rate insufficient to increase the pH above the desired level (e.g., 8.5 or preferably 7.2). Thus, the feeds should be suitably coordinated so as to maintain the pH of the reaction mixture within the ranges specified herein.

While on the subject of pH control, some additional points are worthy of consideration. First of all, operations at low pH (i.e., in the range of about 5.5 to about 6.5) while technically feasible, are less desirable from an economic standpoint because an unnecessarily excessive amount of the halogen is present in the reaction mixture. In addition, it is possible that some depreciation in product quality may be encountered under such more acidic conditions. On the other hand, operations in which the pH drifts above about 8.5 for any significant length of time are not desirable because in general the solubility of the desired product in the aqueous reaction mixture tends to increase under such elevated pH conditions. Under idealized operating conditions, which seldom, if ever, can be achieved in plant scale operations, the process would be conducted at precisely a pH of 7.0. However, as a practical matter, deviation from such ideal condition will inevitably be encountered. Thus, in fine, tuning an operation utilizing a process of this invention, one should strive to provide throughout at least most of the reaction time, a very slight stoichiometric excess of the halogen source relative to the N-halogenatable compound to ensure achievement of complete halogenation to the desired level. For example, if monohalogenation of an N-halogenatable compound having more than one halogenatable nitrogen atom is desired, it is preferable to maintain in the reaction mixture during substantially the entire time the feeds are being carried out slightly more than one equivalent of the halogen relative to the N-halogenatable compound. Similarly, if multi-halogenation of an N-halogenatable compound having more than one halogenatable nitrogen atom is desired, in order to minimize underhalogenation, slightly more than the number of equivalents of halogen atoms to be introduced into the N-halogenatable compound should be employed, and should be maintained in the reaction mixture during substantially the entire time the feeds are being carried out.

The proportions of brominating agent and/or chlorinating agent relative to the N-halogenatable compound should be such that there are in the range of about 1.9 to about 2.1 atoms of the halogen per halogenatable amido or imido nitrogen atom to be halogenated. Thus in the case of 5,5-dihydrocarbylhydantoins such as 5,5-dimethylhydantoin the proportions concurrently being fed to the reaction zone are such that there are in the range of about 3.8 to about 4.2 atoms of halogen per molecule of the 5,5-dialkylhydantoin. As previously noted, under ideal conditions the number of atoms of halogen per amido or imido nitrogen atoms to be halogenated would be precisely that amount required to produce the desired product without any deviation whatsoever from the selected stoichiometry. The fact that the foregoing ranges dip below and extend above such an ideal ratio simply reflects the fact that under actual large scale plant operating conditions, one can operate at slightly below the ideal ratio or slightly above the ideal ratio without material adverse effect relative to the optimum results achievable under such conditions. To the extent possible, it is preferable to operate with a slight excess of the halogen relative to the N-halogenatable compound in the reaction mixture (i.e., in the range of about 2.0 to about 2.1 atoms of halogen per halogenatable amido or imido nitrogen atom to be halogenated) rather than operating continuously in the range of about 2.0 to about 1.9. This ensures full halogenation to the extent desired without use of excessive halogen and consequent loss of raw materials.

Thus, when using bromine or generating bromine in situ and forming a product of white coloration such as 1,3-dibromo-5,5-dimethylhydantoin, a convenient way of monitoring the rate of bromine addition or generation is to feed or generate the bromine at a rate such that the color of the reaction mixture is bright yellow to reddish yellow. The appearance of a reaction mixture having a reddish coloration would indicate that an excessive amount of bromine is present. Other ways of monitoring the halogen present can be used if desired, such as by use of pH meters, chemical pH indicators, and/or the like. Also the halogen feed or generation can be monitored by combinations of any two or more suitable methods for determining pH, such as a combination of color observations as described earlier in this paragraph, and use of one or more pH meters, concurrently or sequentially, or in any other suitable manner. If a combination of two or more ways of measuring pH are used, and if by chance disparate pH measurements result, one should rely upon the method previously determined in actual practice to give the most accurate and reproducible results. Use of carefully calibrated commercially-available pH meters is currently believed to be one of the most reliable ways of determining pH, but it is not intended that the scope of this invention be limited to use of pH meters.

Still another feature of this invention is that the concurrent feeding of the components enables the maintenance within the reactor of an aqueous reaction mixture of sufficiently low concentration that the reaction can be conducted at elevated temperatures (e.g., 40 to about 90° C.) without material decomposition of most N-halogenatable compounds or the N-halogenated products thereof, depending of course upon the thermal decomposition temperature of the particular compound being utilized. In sharp contrast, heretofore it has been commonplace to cool the reactor to temperatures as low as about 5° C. in order to ameliorate the problem of decomposition due to presence of excessive base in the system to which the halogen is added. Pursuant to this invention, it is preferred when operating in a continuous mode to feed the components from which the aqueous reaction mixture is composed in amounts such that the ratio of (i) the volume of the aqueous reaction mixture in liters to (ii) the moles of N-halogenatable compound being fed to the reaction mixture per minute is in the range of about 10 to about 100 liters per mole per minute, and preferably in the range of about 30 to about 60 liters per mole per minute. Similarly, when operating in a batch mode wherein the feeds are to at least one reactor, until the volume of the reaction mixture reaches 50 percent of the total volume of the reactor(s), the feeds to the reaction mixture are maintained such that the ratio of (i) the volume of the reaction mixture in liters to (ii) the moles of the N-halogenatable compound being fed to the reaction mixture per minute is in the range of about 10 to about 100 liters per mole per minute, and preferably in the range of about 20 to about 80 liters per mole per minute. Then, when the volume of the reaction mixture is 50 percent more of the total volume of the reactor(s), the feeds to the reaction mixture are such that the ratio of (i) the volume of the reaction mixture in liters to (ii) the moles of the N-halogenatable compound being fed to the reaction mixture per minute is in the range of about 30 to about 60 liters per mole per minute. By operating a continuous, semi-batch, or batch process using the foregoing ratios, the N-halogenatable compound and the N-halogenated derivative thereof are less susceptible at essentially neutral pH conditions (e.g., 6.8-7.2) to thermal decomposition from the heat of reaction.

In conducting the processes of this invention, the reaction temperatures can be varied within a reasonable range. Typically, the reaction temperature will fall within the range of about 0 to about 90° C. although under some conditions departures from this temperature range may prove acceptable under particular circumstances. Oftentimes temperatures in the range of about 20 to about 80° C. or 90° C. will be found more efficacious. However, temperatures within the range of about 30 to about 70° C. are generally preferred inasmuch as reactions performed at these temperatures tend to produce products in the highest yields. It is most preferred to perform the reaction at temperatures in the range of about 40 to about 60° C., especially when utilizing a hydantoin such as 5,5-dimethylhydantoin, and bromine as the halogen source. Temperatures in the range of about 40 to about 60° C. are most preferred because operations conducted within this range produce product of large particle size in high yield at fast reaction rates and in the most cost-effective manner. When conducting the N-halogenation reaction at temperatures above the boiling temperature of the halogen being fed, it is desirable to feed the halogen subsurface to the liquid phase of the aqueous reaction mixture. In such a case, it is particularly desirable to feed the halogen diluted with an inert gas.

Typically the aqueous reaction mixtures of this invention will be formed, in essence, from four types of components, viz., the N-halogenatable compound, the brominating agent and/or chlorinating agent, the inorganic base, and water. Although it is preferable to minimize the number of components in the aqueous reaction mixture, it is possible to include one or more additional components in such mixtures, provided of course that such other component(s) cause(s) no material deleterious effect on the reaction or precipitate formation. For example, while not ordinarily recommended, it is possible to include certain organic solvents, especially water-miscible organic solvents in the aqueous reaction mixture. Such organic solvent(s) should be in proportions that do not result in a disproportionately large amount of the desired N-halogenated end product remaining in solution, unless of course the solvent is to be subsequently removed, for example, by distillation. At least one potentially beneficial use of an organic solvent involves periodically including one or more organic solvents in the feeds to the reaction zone of the process being operated in a continuous mode in order to dissolve or dislodge encrustations of precipitate that may have built up in the reaction zone. If an organic solvent is to be included in the aqueous reaction mixture, besides not unduly affecting the intended N-halogenation reaction adversely, in the usual situation the solvent should not consume bromine or chlorine. Also, the solvent should not react with the intended N-halogenation product, should not interfere with the in situ generation of bromine (if such is being used), and should not result in formation of an unworkable or overly pasty or sticky precipitate or, in general have any other material adverse effect upon the conduct or further conduct of the process. A few examples of organic solvents that may be considered for use are N,N-dimethylformamide, dimethylsulfoxide, one or more $C_{1-4}$ alkanols, tetrahydrofuran or other saturated ethers, or the like. Therefore, unless expressly stated otherwise, the term "aqueous reaction mixture" as used anywhere in this document, including the claims, does nor exclude the presence of one or more organic solvents, provided no material adverse effect upon the reaction or precipitate formation or product characteristics is caused by the presence of such solvent(s) in the amount in which present relative to the total amount of the overall reaction mixture.

The components of the reaction mixture should be agitated to a sufficient extent so as to avoid localized concentrations of either halogen or base. Thus, for example, in laboratory scale operations, stirring rates in the range of about 300–600 rpm have been found desirable for achieving good mixing within the reaction vessel. In plant scale operations use of a continuously stirred reactor is thus recommended.

Yet another feature of this invention is the fact that the processes can be conducted adiabatically without material reduction in reactor throughput. Thus even when the process is conducted without adding heat energy into the reaction mixture and without recourse to refrigeration, or use of a flowing liquid heat transfer agent, or other ways of cooling (except possibly for normal unassisted heat transfer through the reactor walls to the surrounding atmosphere), the heat buildup from the exothermic reaction can be readily controlled without materially reducing feed rates. Such control can be achieved by maintaining a dilute aqueous reaction mixture, e.g., by operating a continuous, semi-batch, or batch process using the ratios of volume of reaction mixture to moles of N-halogenatable compound being fed per minute as described hereinabove. Despite such dilution, the reaction and precipitate formation nonetheless can proceed rapidly under such adiabatic conditions.

Even though adiabatic operation is possible, when conducting the processes of this invention, especially in a continuous mode, it is preferred to utilize a flow of cooling water or other heat exchange liquid for indirect heat exchange with the reactor contents to ensure maintenance of steady-state temperature conditions in the reaction mixture. If desired, however, the processes of this invention can be conducted using refrigeration.

From the foregoing it can be seen that this invention involves an interrelationship among controllable reaction variables which result in the production of high quality products in high yield in rapid reactions. Thus, this invention features, inter alia, concurrent feeds of the reaction components with specified control of pH by means of feed rates. In preferred embodiments, adjustment and control of temperature enables rapid formation of product in high yield and with large particle size. Also, utilization of reaction mixtures in highly diluted conditions contributes materially, in preferred embodiments, to high yields and allows greater flexibility in operating temperatures. Moreover, the rapid precipitate formation under steady-state conditions makes possible the use of short residence times in continuous operations, and thus contributes materially to improved plant throughput.

As can be readily seen from the Examples hereinafter, this invention makes possible the provision of 1,3-dihalo-5,5-dimethylhydantoins with large average particle sizes. For example, by use of this invention it is now possible to produce 1,3-dibromo-5,5-dimethylhydantoin particulate solids having an average particle size of at least about 175 microns. In fact, 1,3-dibromo-5,5-dimethylhydantoin particulate solids having an average particle sizes of greater than 200, 300, and even as much as over 500 microns have been obtained by use of the present process technology. So far as is known, despite the ability to produce some hydantoin compounds comprised of large particles, 1,3-dibromo-5,5-dimethylhydantoin with an average particle size of 175 microns or greater has not been produced heretofore. Moreover, the 1,3-dihalo-5,5-dimethylhydantoins produced by processes of this invention are devoid of traces of organohalide solvent residues inasmuch as these products are formed in the absence of any halogenated organic solvent such as methylene chloride.

Because this invention enables the direct production of 1,3dibromo-5,5-dimethylhydantoin reaction products in which the recovered 1,3-dibromo-5,5-dimethylhydantoin particulate solids have an average particle size of at least 175 microns, several very substantial advances in the art are made possible. For example, it has been discovered that 1,3-dibromo-5,5dimethylhydantoin particulate solids having average particle sizes above 175 microns:

a) are far easier to handle because of their much lower dusting tendencies;
b) have flow properties through pipes and conduits and from hoppers that are far superior;
c) could be pressure compacted into shape-retentive tablets without use of a binder and without breakage occurring, whereas samples of commercially-available 1,3-dibromo-5,5-dimethylhydantoin particulate solids from several different sources could not be converted into tablets in the same manner without breakage occurring.

These and related discoveries are described in detail in commonly-owned copending Application Ser. No. 09/484,687 referred to above.

The following Examples are presented to illustrate the practice of, and advantages made possible by, this invention. These Examples are not intended to limit, and should not be construed as limiting, the scope of this invention to the particular operations or conditions described therein. In each run of Examples 1-10 and in Example 13, pH was monitored by use of a pH meter, and bromine was fed using a Cole-Parmer Masterflex computerized drive and Easy-Load® pump head. When conducting the continuous operations of Examples 9 and 10, the resulting reaction slurry was collected manually and intermittently from the bottom of the reactor. Each fraction was collected in a 500 mL flask.

EXAMPLE 1

235 Grams of NaOH (5.85 mol) are dissolved in 1800 g of water, and 375 g of 5,5-dimethylhydantoin (2.93 mol) is added to the NaOH solution. There are 935 g of $Br_2$ (5.85 mol) in the bromine reservoir. A 1-liter jacketed flask into which the $Br_2$ and the 5,5-dimethylhydantoin/NaOH solution are fed is maintained at 25° C. with a cooling bath. The 5,5dimethylhydantoin/NaOH solution is co-fed to the reaction flask simultaneously with, but separately from, $Br_2$. The feed of the 5,5-dimethylhydantoin/NaOH solution was initiated shortly before (e.g., 3–4 min.) the initiation of the $Br_2$ feed. The feed rate of the 5,5-dimethylhydantoin/NaOH solution is 10 mL/minute, and the feed rate of the $Br_2$ is 1.60–1.70 mL/minute. The reaction mixture is stirred with a mechanical stirrer at a rate of350–400 rpm. During the reaction, the pH ranged from 7.4 to 7.9. The slurry that forms as the reaction progresses is collected at a rate such that the level of the solution in the reaction flask remains constant. 500 mL fractions of product are collected through the bottom of the reaction flask, in an average time of 30 minutes per fraction. When the 5,5-dimethylhydantoin/

NaOH solution feed is finished, 86 g of Br$_2$ (0.54 mol) remains in the bromine reservoir.

Each product fraction is filtered and washed with three 500 mL portions of water, and the solid is then dried under a stream of nitrogen. The isolated yield of 1,3-dibromo-5,5-dimethylhydantoin is 673 g, a yield of 80% based on 5,5-dimethylhydantoin, or a yield of 89% based on Br$_2$. The active bromine content is at least 99%, as determined by iodometric titration.

EXAMPLE 2

44 Grams of NaOH (1.1 mol) are dissolved in 338 g of water, and 70.4 g of 5,5-dimethylhydantoin (0.55 mol) is added to the NaOH solution. There are 175.1 g of Br$_2$ (1.1 mol) in the bromine reservoir. The reaction flask into which the Br$_2$ and the 5,5-dimethylhydantoin/NaOH solution are fed is maintained at 35° C. with a heating bath. The reaction flask is charged with ~200 mL heel (238 g) of a 1,3-dibromo-5,5-dimethylhydantoin filtrate (mother liquor). The 5,5-dimethylhydantoin/NaOH solution is co-fed to the reaction flask simultaneously with, but separately from, Br$_2$. The reaction mixture is stirred with a mechanical stirrer at a rate of 400 rpm. During the reaction, the pH ranged from 6.9 to 8.2. The reaction temperature stabilized at 37° C. during the 0.5 hour addition time. When the addition of reagents is finished, the orange slurry is filtered at 35° C. and washed with 650 mL of water. The resultant white solid is dried overnight under a stream of nitrogen. The isolated yield of 1,3-dibromo-5,5-dimethylhydantoin is 147.6 g, a yield of 94%, and the active bromine content of the 1,3-dibromo-5,5-dimethylhydantoin is 55.1 wt % (98.6% of the theoretical value), as determined by iodometric titration.

EXAMPLE 3

44 Grams of NaOH (1.1 mol) are dissolved in 338 g of water, and 70.4 g of 5,5-dimethylhydantoin (0.55 mol) is added to the NaOH solution. There are 172.0 g of Br$_2$ (1.07 mol) in the bromine reservoir. The reaction flask into which the Br$_2$ and the 5,5-dimethylhydantoin/NaOH solution are fed is maintained at 67° C. with a heating bath. The reaction flask is charged with ~200 mL heel (238 g) of a 1,3-dibromo-5,5-dimethylhydantoin filtrate (mother liquor). The 5,5-dimethylhydantoin/NaOH solution is co-fed to the reaction flask simultaneously with, but separately from, Br$_2$. The bromine is diluted with nitrogen and fed below the surface of the solution in the reaction flask. The reaction mixture is stirred with a mechanical stirrer at a rate of 400 rpm; the pH ranged from 6.7 to 7.1 during the reaction. During the 0.5 hour addition time, the reaction temperature stabilized at 67° C. When the addition of reagents is finished, the orange slurry is discharged from the reaction flask into a beaker and allowed to cool slowly. The slurry is filtered at 45° C. and washed with two 500 mL portions of water. The resultant white solid is dried overnight under a stream of nitrogen. The isolated yield of 1,3-dibromo-5,5-dimethylhydantoin is 130.5 g, a yield of ~83% based on 5,5-dimethylhydantoin, or a yield of ~85% based on Br$_2$. The active bromine content of the 1,3-dibromo-5,5-dimethylhydantoin is 55.9 wt % (100% of the theoretical value), as determined by iodometric titration. Particle size data on the 1,3-dibromo-5,5-dimethylhydantoin product formed in this operation based on a representative dried sample of the product are summarized in Table 1.

TABLE 1

| Particle Size Category | Particle Size of Product |
| --- | --- |
| Average | 237.5μ |
| 10% is greater than | 371.6μ |
| 25% is greater than | 309.8μ |
| 50% is greater than | 239.1μ |
| 75% is greater than | 165.6μ |
| 90% is greater than | 99.81μ |
| Range | 0.040–541.9μ |

EXAMPLE 4

354 Grams of NaOH (8.85 mol) are dissolved in 2700 g of water. 562 g of 5,5-dimethylhydantoin (4.386 mol) is added to the NaOH solution. The reaction flask is charged with 500 mL heel of a 1,3-dibromo-5,5 dimethylhydantoin filtrate (mother liquor). The 5,5-dimethylhydantoin/NaOH solution is co-fed to the jacketed reaction flask, no heating or cooling is applied simultaneously with, but separately from, Br$_2$. The feed rate of the 5,5-dimethylhydantoin/NaOH solution is 10 mL/minute, and the feed rate of the Br$_2$ is initially 1.70 mL/minute, but is adjusted later to 1.68 mL/minute to maintain the pH of the reaction mixture at ~7.0. The reaction mixture is stirred with a mechanical stirrer at a rate of 400 rpm reaction temperature is stabilized at about 42° C. The slurry that forms as the reaction progresses is collected at a rate such that the level of the solution in the reaction flask remains constant. Eight 500 mL fractions of product were collected through the bottom of the reaction flask, in an average time of 30 minutes per fraction. A total of 1374.5 g of Br$_2$ (8.59 mol) are added during the reaction.

Each product fraction is filtered and washed with a 500 mL portion of water; the solids are then dried overnight at 50° C. in a vacuum oven. The total isolated yield of 1,3-dibromo-5,5-dimethylhydantoin is 1152 g, a yield of 92% based on 5,5-dimethylhydantoin, or a yield of 94% based on Br$_2$. The active bromine content of the 1,3-dibromo-5,5-dimethylhydantoin ranges from 55.4 wt % to 55.7 wt % (99.1% to 99.7% of the theoretical value), as determined by iodometric titration. The average particle size of the 1,3-dibromo-5,5-dimethylhydantoin is greater than 150μ.

EXAMPLE 5

89 Grams of NaOH (2.2 mol) are dissolved in 676 g of water, and 141 g of 5,5-dimethylhydantoin (1.1 mol) is added to the NaOH solution. There are 350 g of Br$_2$ (2.2 mol) in the bromine reservoir. The reaction flask into which the Br$_2$ and the 5,5-dimethylhydantoin/NaOH solution are fed is maintained at 67° C. with a heating bath. The reaction flask is charged with ~400 mL heel (483 g) of a 1,3-dibromo-5,5-dimethylhydantoin filtrate (mother liquor). The 5,5-dimethylhydantoin/NaOH solution is co-fed to the reaction flask simultaneously with, but separately from, Br$_2$. The reaction mixture is stirred with a mechanical stirrer at a rate of 400 rpm. During the reaction, the pH ranged from 6.8 to 7.1. The reaction temperature stabilized at 67° C. during the 66 minute addition time. When the addition of reagents is finished, the orange slurry is filtered at 43° C. and washed with 1000 mL (2×500 mL) of water. The resultant white solid is dried overnight under a stream of nitrogen. 307.3 Grams of Br$_2$ (1.92 mol) had been fed to the reaction flask. The isolated yield of 1,3-dibromo-5,5-dimethylhydantoin is 212.5 g, a yield of 77% based on Br$_2$, and 68% based on 5,5-dimethylhydantoin; the active bromine content of the 1,3-dibromo-5,5-dimethylhydantoin is 55.9 wt % (100% of the theoretical value), as determined by iodometric titration.

EXAMPLE 6

88 Grams of NaOH (2.2 mol) are dissolved in 338 g of water, and 140.8 g of 5,5-dimethylhydantoin (1.1 mol) is added to the NaOH solution. There are 352 g of $Br_2$ (2.2 mol) in the bromine reservoir. The reaction flask into which the $Br_2$ and the 5,5-dimethylhydantoin/NaOH solution are fed is maintained at 69° C. with a heating bath. The reaction flask is charged with ~200 mL heel (240 g) of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The reaction mixture is stirred with a mechanical stirrer at a rate of 400 rpm. During the reaction, the pH ranged from 6.8 to 7.0. The reaction temperature stabilized at 68–69° C. during the 39 minute addition time. When the addition of reagents is finished, the orange slurry is filtered at 40° C. and washed with 500 mL of water. The resultant white solid is dried overnight under a stream of nitrogen. 285.5 Grams of $Br_2$ (1.78 mol) had been fed to the reaction flask. The isolated yield of 1,3-dibromo-5,5-dimethylhydantoin is 186.8 g, a yield of 73% based on $Br_2$, and 60% based on 5,5-dimethylhydantoin; the active bromine content of the 1,3-dibromo-5,5dimethylhydantoin is 53.4 wt % (96% of the theoretical value), as determined by iodometric titration.

Table 2 summarizes the particle size data for the products of Examples 5 and 6.

TABLE 2

| Particle Size Category | Particle Size of Product - Example 5 | Particle Size of Product - Example 6 |
| --- | --- | --- |
| Average | 210.4μ | 293.6μ |
| 10% is greater than | 381.7μ | 451.2μ |
| 25% is greater than | 298.3μ | 349.6μ |
| 50% is greater than | 196.8μ | 256.3μ |
| 75% is greater than | 115.3μ | 174.9μ |
| 90% is greater than | 56.86μ | 110.6μ |
| Range | 0.040–594.9μ | 0.040–>2000μ |

EXAMPLE 7

44.2 Grams of NaOH (1.1 mol) are dissolved in 338 g of water, and 70.4 g of 5,5-dimethylhydantoin (0.55 mol) is added to the NaOH solution. There are 173 g of $Br_2$ (1.08 mol) in the bromine reservoir. The reaction flask into which the $Br_2$ and the 5,5-dimethylhydantoin/NaOH solution are fed is maintained at 57° C. with a heating bath. The reaction flask is charged with ~200 mL heel (244 g) of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The reaction mixture is stirred with a mechanical stirrer at a rate of 400 rpm. During the reaction, the pH ranged from 6.8 to 7.2. Maintenance of the desired pH was accomplished by adjusting the bromine feed rate. The reaction temperature stabilized at 57° C. during the 33 minute addition time. When the addition of reagents is finished, the orange slurry is filtered at 38° C. and washed with 500 mL of water. The resultant white solid is dried overnight under a stream of nitrogen. The isolated yield of 1,3-dibromo-5,5-dimethylhydantoin is 139.8 g, a yield of 91% based on $Br_2$, and 89% based on 5,5-dimethylhydantoin; the active bromine content of the 1,3-dibromo-5,5-dimethylhydantoin is 55.7 wt % (99.7% of the theoretical value), as determined by iodometric titration.

EXAMPLE 8

44.2 Grams of NaOH (1.1 mol) are dissolved in 338 g of water, and 70.3 g of 5,5-dimethylhydantoin (0.55 mol) is added to the NaOH solution. There are 172.5 g of $Br_2$ (1.08 mol) in the bromine reservoir. The reaction flask into which the $Br_2$ and the 5,5-dimethylhydantoin/NaOH solution are fed is maintained at 48° C. with a heating bath. The reaction flask is charged with ~200 mL heel of a 1,3dibromo-5,5-dimethylhydantoin filtrate (mother liquor). The 5,5-dimethylhydantoin/NaOH solution is co-fed to the reaction flask simultaneously with, but separately from, $Br_2$. The reaction mixture is stirred with a mechanical stirrer at a rate of 400 rpm. During the reaction, the pH ranged from 6.8 to 7.2., Maintenance of the desired pH was accomplished by adjusting the bromine feed rate. The reaction temperature stabilized at 48° C. during the 34 minute addition time. When the addition of reagents is finished, the orange slurry is filtered at 38° C. and washed with 500 mL of water. The resultant white solid is dried overnight under a stream of nitrogen. The isolated yield of 1,3dibromo-5,5-dimethylhydantoin is 144.8 g, a yield of 94% based on $Br_2$, and 92% based on 5,5-dimethylhydantoin; the active bromine content of the 1,3-dibromo-5,5-dimethylhydantoin is 55.0 wt % (98.4% of the theoretical value), as determined by iodometric titration.

The particle size data for the products of Examples 7 and 8 are summarized in Table 3.

TABLE 3

| Particle Size Category | Particle Size of Product - Example 7 | Particle Size of Product - Example 8 |
| --- | --- | --- |
| Average | 231.2μ | 178.4μ |
| 10% is greater than | 338.3μ | 281.1μ |
| 25% is greater than | 285.0μ | 230.9μ |
| 50% is greater than | 228.8μ | 175.7μ |
| 75% is greater than | 177.8μ | 125.0μ |
| 90% is greater than | 133.0μ | 79.14μ |
| Range | 0.040–493.6μ | 0.040–409.6μ |

EXAMPLE 9

The process of this Example was conducted in a continuous fashion. A feed solution of 5,5-dimethylhydantoin/NaOH was formed by adding 5,5-dimethylhydantoin to a 9 wt % NaOH solution, such that the 5,5dimethylhydantoin concentration was about 1.1 M. The 5,5-dimethylhydantoin/NaOH solution was co-fed to the reaction flask simultaneously with, but separately from, $Br_2$. The flask was suspended in a heating bath. The reaction mixture was stirred with a mechanical stirrer at a rate of 500 rpm. The reaction mixture was maintained at a pH of about 7.0±0.2, and the reaction temperature was maintained at 55° C. Ten fractions of product were collected in an average time of 30 minutes per fraction. The isolated yield of the 1,3-dibromo-5,5-dimethylhydantoin was 90% based on 5,5-dimethyihydantoin, and 92% based on added $Br_2$. The purity of the 1,3-dibromo-5,5-dimethylhydantoin, a white crystalline product, was 99.8%, based on the theoretical bromine content. Fractions 5–10 represent the particle size of the product as formed during steady-state operating conditions. Table 4 summarizes average particle size data and particle size distribution data relating to fractions 5–10 based on samples of each such fraction taken during the steady-state operation of the continuous process. The determinations showed that a bimodal distribution of the product had been produced. The overall average particle size of the product was 512.3 microns.

TABLE 4

| Particle Size | Fraction 5 | Fraction 6 | Fraction 7 | Fraction 8 | Fraction 9 + 10 |
|---|---|---|---|---|---|
| Average | 371.7µ | 445.6µ | 535.5µ | 560.3µ | 545.9µ |
| 10% is greater than | 530.7µ | 626.0µ | 724.7µ | 805.0µ | 952.1µ |
| 25% is greater than | 462.2µ | 550.9µ | 643.3µ | 729.3µ | 833.4µ |
| 50% is greater than | 386.0µ | 474.5µ | 559.7µ | 641.8µ | 676.7µ |
| 75% is greater than | 256.8µ | 369.6µ | 447.8µ | 436.1µ | 149.6µ |
| 90% is greater than | 94.76µ | 134.4µ | 150.3µ | 94.5µ | 76.02µ |
| Range | 0.791–786.9µ; 1255–1512µ | 4.241–786.9µ; 1143–1255µ | 3.519–863.9µ; 1143–1512µ | 3.519–8.639µ; 1143–1512µ | 0.721–409.6µ; 493.6–1255µ |

EXAMPLE 10

Another continuous operation was conducted in a manner similar to that of Example 9. The feed solution was formed by dissolving 355 g (8.87 mols) in 3550 g of water. To this was added 560 g (4.37 mols) of 5,5-dimethylhydantoin. The concurrent feeds were adjusted to maintain the pH of the aqueous reaction mixture at 7.0±0.2. The temperature was maintained at 55° C. The total amount of bromine ($Br_2$) fed was 1359.4 g (8.50 mols). As in Example 9, ten fractions of the reaction mixture were collected. However, in this operation, the addition rates were adjusted such that the average residence time was approximately 1 hour per fraction. The total isolated yield of 1,3-dibromo-5,5-dimethylhydantoin was 88% based on 5,5-dimethylhydantoin used and 90% based on the added bromine. The 1,3-dibromo-5,5-dimethylhydantoin product was obtained as a white crystalline solid. Table 5 summarizes the average particle size data and product distribution data relating to the product formed in this reaction. Fractions 5–10 represent the particle size of the product as formed during steady-state operating conditions. As in Example 9, the product formed was bimodal. In Table 5 "n.d." indicates that the particle size determination for the larger particle sized fraction was not determined; the instrument used could not measure particles having a particle size greater than 200 microns. The overall average particle size of the product was at least 455.5 microns.

TABLE 5

| Particle Size | Fraction 5 | Fraction 6 | Fraction 7 | Fraction 8 | Fraction 9 + 10 |
|---|---|---|---|---|---|
| Average | 421.2µ | 478.6µ | 494.0µ | 536.6µ | 631.9µ |
| 10% is greater than | 606.5µ | 699.1µ | 781.7µ | 1063µ | 1438µ |
| 25% is greater than | 532.1µ | 623.4µ | 651.5µ | 813.9µ | 995.7µ |
| 50% is greater than | 452.3µ | 535.0µ | 548.5µ | 546.7µ | 522.8 |
| 75% is greater than | 340.0µ | 372.2µ | 176.6µ | 150.3µ | 160.7µ |
| 90% is greater than | 140.8µ | 112.8µ | 68.94µ | 72.93 | 81.68µ |
| Range | 2.423–786.9µ; n.d. | 2.423–863.9µ; n.d. | 1.520–863.9µ; 1255–1512µ | 0.04–2000µ; n.d. | 0.04–>2000µ; n.d. |

EXAMPLE 11

Samples of commercially-available N,N'-dihalo-5,5-dimethylhydantoins were obtained and subjected to standard test procedures in order to determine their average particle size using the Coulter® LS Particle Size Analyzer. Table 6 summarizes the results of these average particle size determinations, and also sets forth the data obtained in the same way on a representative sample of the 1,3-dibromo-5,5-dimethylhydantoin product of this invention produced in Example 4. Table 7 summarizes the particle size distribution data on the commercially-available 1,3-dihalo-5,5-dimethylhydantoins. In Table 7 the following abbreviations are used: DCDMH is 1,3-dichloro-5,5-dimethylhydantoin; BCDMH is N,N'-bromochloro-5,5-dimethylhydantoin; and DBDMH is 1,3-dibromo-5,5-dimethylhydantoin.

TABLE 6

| N,N'-dihalo-5,5-dimethylhydantoin | Source | Average Particle Size |
|---|---|---|
| 1,3-dichloro-5,5-dimethylhydantoin | Aldrich Chemical Co. | 108.1 microns |
| N,N'-bromochloro-5,5-dimethylhydantoin | Aldrich Chemical Co. | 323.8 microns |
| 1,3-dibromo-5,5-dimethylhydantoin | Aldrich Chemical Co. | 162.1 microns |
| 1,3-dibromo-5,5-dimethylhydantoin | Albemarle Corporation | 64.5 microns |
| 1,3-dibromo-5,5-dimethylhydantoin | Great Lakes Chemical Corporation | 45.2 microns |
| 1,3-dibromo-5,5-dimethylhydantoin | The present process | 293.6 microns |

TABLE 7

| Particle Size | DCDMH - Aldrich | BCDMH - Aldrich | DBDMH - Aldrich | DBDMH - Albemarle | DBDMH - Great Lakes |
|---|---|---|---|---|---|
| Average | 108.1µ | 323.8µ | 162.1µ | 64.59µ | 45.23µ |
| 10% is greater than | 195.3µ | 877.9µ | 359.2µ | 162.7µ | 78.76µ |
| 25% is greater than | 134.4µ | 409.9µ | 177.6µ | 90.12µ | 49.76µ |
| 50% is greater than | 80.07µ | 173.9µ | 86.03µ | 39.21µ | 34.68µ |
| 75% is greater than | 45.99µ | 65.39µ | 47.37µ | 26.85µ | 23.25µ |
| 90% is greater than | 27.19µ | 29.35µ | 27.67µ | 17.91µ | 13.90µ |
| Range | 0.04–>2000µ | 0.04–>2000µ | 0.04–>2000µ | 0.04–309.6µ | 0.04–409.6µ |

EXAMPLE 12

The color characteristics of samples of the bromine-containing N,N'-dihalo-5,5-dimethylhydantoins referred to in Example 6 were determined using Hunter Lab Color Quest Model 450 instrument. The test determined the Yellowness Index of the powder using the foregoing instrument which is approved for use in accordance with ASTM test designation E 313–96 "Standard Practice for Calculating Yellowness and Whiteness Indices from Instrumentally Measured Color Coordinates". The instrument includes a station for receiving a crucible filled with the powder to be tested for its color characteristics, and a pair of light sources disposed above the crucible. A first such light source is spaced and positioned directly above the surface of the crucible and its contents so as to direct a beam of light at a 90° angle relative to the horizontal upper surface of the contents of the crucible. The second such light source is spaced and positioned so as to direct a beam of light at a 45° angle relative to the horizontal upper surface of the contents of the crucible. One photomultiplier detector is positioned directly above the first such light source so as to receive the reflected light from the surface receiving the beam of light from the first light source. Another photomultiplier detector is positioned at a 90° angle relative to the beam of light issuing from the second light source so as to receive the reflected light from the surface receiving the beam of light from the second light source. Each such photomultiplier measures the wavelength and the amount of the reflected beam and inputs such data to a microprocessor programmed to calculate from such data a value for the Yellowness Index of the powder. The results of these evaluations in terms of such Yellowness Indices (YI) are summarized in Table 8. The higher the numerical value of the Yellowness Index, the more yellow the product.

TABLE 8

| N,N'-dihalo-5,5-dimethylhydantoin | Source | Yellowness Index |
|---|---|---|
| N,N'-bromochloro-5,5-dimethylhydantoin | Aldrich Chemical Co. | 12.82 |
| 1,3-dibromo-5,5-dimethylhydantoin | Aldrich Chemical Co. | 37.82 |
| 1,3-dibromo-5,5-dimethylhydantoin | Albemarle Corporation | 31.22 |
| 1,3-dibromo-5,5-dimethylhydantoin | Great Lakes Chemical Corporation | 21.28 |
| 1,3-dibromo-5,5-dimethylhydantoin | The present invention | 11.65 |

EXAMPLE 13

Another continuous operation was performed using a glass reactor into which were concurrently fed, on a continuous basis, an aqueous solution formed from 5,5-dimethylhydantoin and NaOH, and a separate feed of bromine. The aqueous solution was made by adding 5,5-dimethylhydantoin to an aqueous 9 wt % NaOH solution. This solution contained about 22.4 wt % of 5,5-dimethylhydantoin and 7 wt % NaOH. A one liter, jacketed reactor having an interior diameter of 82 millimeters equipped with an anchor agitator, with an outer diameter of 72 millimeters, was used, and a silicone fluid (Rhodersil 4720V20 fluid; Rhone-Poulenc) was circulated through the jacketing. The temperature of the reaction was controlled at 38° C. Both feeds were controlled by pumps; the average feed rate of the 5,5-dimethylhydantoin/NaOH solution was 15.84 grams/minute via a Prominent Gamma G/4A positive displacement pump, and the average feed rate of the bromine was 4.67 grams/minute via a Masterflex Easy-Load peristaltic pump. The reaction mixture was stirred at 400 rpm. The pH of the reaction was monitored by measuring the pH of the effluent using a pH meter, and the pH ranged from 6.06 to 6.36 during the reaction. Product removal from the reactor was also controlled by a pump. Residence time was, on average, 30 minutes per fraction; each fraction was about 500 mL. A yield of 90.5% of 1,3-dibromo-5,5-dimethylhydantoin was obtained, based on the amount of 5,5-dimethylhydantoin fed to the reactor. The active bromine content of the 1,3-dibromo-5,5-dimethylhydantoin was >55.3%, as determined by standard iodometric titration. Thus, the purity of this product was greater than 99.0%.

Table 9 summarizes particle size data on the 1,3-dibromo-5,5-dimethylhydantoin product formed in the continuous operation of Example 13. These data are averaged data based on two samples taken at different times during the continuous operation once steady state conditions, or essentially steady state conditions, had been achieved.

TABLE 9

| Particle Size Category | Particle Size of Product |
|---|---|
| Average | 188.9µ |
| 10% is greater than | 295.2µ |
| 25% is greater than | 255.6µ |
| 50% is greater than | 203.1µ |
| 75% is greater than | 122.5µ |
| 90% is greater than | 55.9µ |
| Range | 0.872–356.5µ |

As used in this document, the term "water-soluble" means that the substance being described has at least sufficient solubility in water to form an aqueous solution containing at least a sufficient amount of such dissolved substance (presumably in ionized form) to enable the operation in which such solution is being used, to be carried out under the particular conditions in which the solution is being employed. Naturally it is desirable that the substance have a greater solubility in water than this in water under such conditions. However, the term does not mean that the substance must dissolve in all proportions in water under such conditions.

Compounds referred to by chemical name or formula anywhere in this document, whether referred to in the singular or plural, are identified as they exist prior to coming into contact with another substance referred to by chemical name or chemical type (e.g., another component, a solvent, or etc.). It matters not what preliminary chemical changes, if any, take place in the resulting mixture or solution, as such changes are the natural result of bringing the specified substances together under the conditions called for pursuant to this disclosure. Also, even though the claims may refer to substances in the present tense (e.g., "comprises", "is", etc.), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise.

It will also be understood that the terms "substantial" and "substantially" denote that chemical processes ordinarily do not involve absolutes. Thus instead of describing a variable as an absolute, it is far more realistic to describe the variable as being in the substantial vicinity of the expressed variable.

For example when describing a stoichiometric quantity it is far more realistic to refer to the quantity as being substantially a stoichiometric quantity since one skilled in the art fully realizes that slight deviations from the absolute stoichiometry would produce no appreciable difference in results. Thus in any and all respects, this document should be read with the application of common sense.

Each and every patent or publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process for the production of 1,3-dibromo-5,5-dimethylhydantoin, which process comprises concurrently, or substantially concurrently, feeding into a reaction zone:
   A)
   separate feeds of (i) an aqueous solution or slurry formed from an inorganic base and 5,5-dimethylhydantoin, and (ii) a brominating agent; or
   B)
   at least three separate feeds, one of which is a brominating agent, and at least two other feeds, at least one of which is selected from (a) and (b); and at least one of which is selected from (c) and (d), wherein
   (a)
   is an aqueous solution or slurry formed from an inorganic base,
   (b)
   is an aqueous solution or slurry formed from an inorganic base and 5,5-dimethylhydantoin,
   (c) is 5,5-dimethylhydantoin, and
   (d)
   is an aqueous solution or slurry formed from 5,5-dimethylhydantoin; in proportions such that 1,3-dibromo-5,5dimethylhydantoin is continuously or substantially continuously formed and precipitates in the liquid phase of an aqueous reaction mixture during all or substantially of the time said concurrent feeding is occurring, and such that the pH of said liquid phase is continuously or substantially continuously maintained in the range of about 5.5 to about 8.5 during all or substantially all of the time said concurrent feeding is occurring.

2. A process of claim 1 wherein said aqueous reaction mixture is at one or more temperatures in the range of about 40 to about 60° C.

3. A process of claim 1 wherein said pH is in the range of about 6.5 to about 8.5, and wherein the brominating agent used is bromine.

4. A process of claim 1 wherein at least said 5,5-dimethylhydantoin and said inorganic base are fed in the form of a single preformed aqueous solution or slurry.

5. A process of claim 1 wherein at least said 5,5-dimethylhydantoin is fed in the form of a separate preformed aqueous solution or slurry, and wherein at least said inorganic base is fed in the form of a separate preformed aqueous solution or slurry.

6. A process of claim 1 wherein when starting up said process, said feeding is initiated into a reactor containing (i) a solids-containing heel of a reaction mixture from a prior reaction in which the product to be formed had been formed, or (ii) a solids-free mother liquor of a reaction mixture from a prior reaction in which the product to be formed had been formed.

7. A process of claim 1 wherein said feeding is initially to a mixing device which produces an effluent stream formed A)
said 5,5-dimethylhydantoin and said inorganic base; or
B) (i) said 5,5-dimethylhydantoin and water, (ii) said inorganic base and water, or (iii) said brominating agent and water; or
C) said 5,5-dimethylhydantoin, said inorganic base, and water; and wherein the effluent stream is fed into a reaction vessel containing a larger volume of the aqueous reaction mixture; wherein said stream is subjected to dilution in the aqueous reaction mixture before the temperature of said effluent stream exceeds about 90° C.; and wherein the temperature of the aqueous reaction mixture is maintained in the range of about 0 to about 90° C. during all or substantially all of the time said feeding is occurring.

8. A process of claim 7 wherein said mixing device is a static mixer, and wherein the effluent seam from the mixer is being fed subsurface to the liquid phase of the aqueous reaction mixture.

9. A process of claim 7 wherein said mixing device is a jet mixer producing a high velocity stream, which stream is being fed subsurface to the liquid phase of the aqueous reaction mixture.

10. A process of claim 1 wherein said aqueous reaction mixture is at one or more temperatures in the range of about 0 to about 90° C.

11. A process of claim 1 wherein said inorganic base is a basic salt or oxide of a water-soluble alkali metal or an alkaline earth metal; wherein the amount of such base is the stoichiometric quantity, or is substantially the stoichiometric quantity, theoretically required to deprotonate the nitrogen atoms of said 5,5-dimethylhydantoin; wherein said brominating agent is (i) bromine, (ii) an alkali metal bromide or aqueous solution thereof, or an alkaline earth metal bromide or aqueous solution thereof, and chlorine, or hypochlorite salt or aqueous hypochlorite solution in amounts sufficient to generate bromine in situ, or (iii) a combination of (i) and (ii); wherein at least all or such portion of said brominating agent that is in the vapor state, if any, is fed subsurface to the liquid phase of the aqueous reaction mixture; wherein the temperature of the aqueous reaction mixture is continuously or substantially continuously in the range of from about 30 to about 90° C. during all or substantially all of the time said feeding is occurring; and wherein the proportions of the feeds are such that the total amount of said brominating agent being fed to N-halogenate the 5,5-dimethylhydantoin being fed are such that there are in the range of about 3.8 to about 4.2 atoms of bromine per molecule of 5,5-dimethylhydantoin.

12. A process of any of claims 1, 3, or 10 wherein said process is conducted in a continuous mode in which, under steady state conditions, said feed(s) are maintained such that the ratio of (i) the volume of said reaction mixture in liters to (ii) the moles of 5,5-dimethylhydantoin being fed to the reaction mixture per minute is in the range of about 10 to about 100 liters per mole per minute.

13. A process of any of claims 1, 3, or 10 wherein said process is conducted in batch mode in at least one reactor and wherein, until the volume of the reaction mixture reaches 50 percent of the total volume of the reactor(s), the feeds to said reaction mixture are maintained such that the ratio of (i) the volume of said reaction mixture in liters to (ii) the moles of 5,5-dimethylhydantoin being fed to the reaction mixture per minute is in the range of about 10 to about 100 liters per mole per minute; and wherein, when the volume of the reaction mixture is 50 percent or more of the total volume of the reactor(s), the feeds to said reaction mixture are maintained such that the ratio of (i) the volume of said reaction mixture in liters to (ii) the moles of 5,5-dimethylhydantoin being fed to the reaction mixture per minute is in the range of about 30 to about 60 liters per mole per minute.

14. A process of claim 1 wherein said pH is in the range of about 6.5 to about 8.5.

15. A process of claim 14 wherein said brominating agent is bromine, and is fed subsurface to the liquid phase of said reaction mixture.

16. A process of claim 14 wherein said brominating agent is (i) an alkali metal bromide or an alkaline earth metal bromide, and (ii) chlorine, a hypochlorite salt, or an aqueous hypochlorite solution in amounts sufficient to generate bromine in situ, and if (ii) is chlorine, at least the chlorine is fed subsurface to the liquid phase of said reaction mixture.

17. A process of claim 14 wherein the inorganic base is a water-soluble basic salt or oxide of an alkali metal or an alkaline earth metal, and wherein the amount of such base is the stoichiometric quantity, or is substantially the stoichiometric quantity, theoretically required to deprotonate the nitrogen atoms of said 5,5-dimethylhydantoin.

18. A process of claim 1 wherein said aqueous reaction mixture is at one or more temperatures in the range of about 0 to about 90° C., and wherein if said brominating agent is in the form of a vapor, said vapor is fed subsurface to the liquid phase of the reaction mixture.

19. A process of any of claims 14, 15, or 16 wherein said process is conducted in a continuous mode in which, under steady state conditions, said feed(s) are maintained such that the ratio of (i) the volume of said reaction mixture in liters to (ii) the moles of 5,5dimethylhydantoin being fed to the reaction mixture per minute is in the range of about 10 to about 100 liters per mole per minute.

20. A process of any of claims 14, 15, or 16 wherein said process is conducted in a batch mode in at least one reactor and wherein, until the volume of the reaction mixture reaches 50 percent of the total volume of the reactor(s), the feeds to said reaction mixture are maintained such that the ratio of (i) the volume of said reaction mixture in liters to (ii) the moles of 5,5dimethylhydantoin being fed to the reaction mixture per minute is in the range of about 10 to about 100 liters per mole per minute; and wherein, when the volume of the reaction mixture is 50 percent or more of the total volume of the reactor(s), the feeds to said reaction mixture are maintained such that the ratio of (i) the volume of said reaction mixture in liters to (ii) the moles of 5,5-dimethylhydantoin being fed to the reaction mixture per minute is in the range of about 30 to about 60 liters per mole per minute.

21. A process of claim 1 wherein said pH is in the range of about 6.8 to about 7.2.

22. A process of claim 21 wherein the temperature of said reaction mixture is in the range of about 20 to about 80° C., and wherein, if all or part of said brominating agent is in the form of a vapor, said vapor is fed subsurface to the liquid phase of said reaction mixture.

23. A process of claim 1 wherein the proportions of water, inorganic base, and 5,5-dimethylhydantoin being fed are such that:
A) where the inorganic base has a monovalent cation, there are from about 0.5 to about 2.5 moles of 5,5-dimethylhydantoin and from about 0.5 to about 2.5 moles of the base, per liter of water; and
B) where the base has a divalent cation, there are about 0.5 to about 2.5 moles of 5,5-dimethylhydantoin and from about 0.25 to about 1.25 moles of the base, per liter of water.

24. A process of claim 1 wherein the proportions of water, inorganic base, and 5,5-dimethylhydantoin being fed are such that:
A) where the inorganic base has a monovalent cation, there are from about 1.0 to about 1.5 moles of 5,5dimethylhydantoin and from about 1.0 to about 1.5 moles of the base, per liter of water; and
B) where the base has a divalent cation, there are about 1.0 to about 1.5 moles of 5,5-dimethylhydantoin and from about 0.5 to about 0.75 moles of the base, per liter of water.

25. A process of claim 1 wherein the process is conducted in a batch mode.

26. A process of claim 25 wherein during at least about 80% of the period of time said concurrent separate feeds are being carried out, precipitate is being formed that has a purity of at least about 97%.

27. A process of claim 1 wherein the process is conducted in a continuous mode; wherein the temperature of the aqueous reaction mixture is in the range of about 20 to about 90° C.; and wherein said inorganic base and 5,5-dimethylhydantoin are fed either as separate solutions or slurries in water or as a single solution or slurry in water.

28. A process of claim 27 wherein during steady-state operation, precipitate is continuously being formed that (1) has a purity of at least about 97%, and (2) is formed in a continuous or substantially continuous yield of at least about 85% based on the amount of the 5,5-dimethylhydantoin being fed to the reactor.

29. A process of claim 2 wherein said process is conducted in a continuous mode in which, under steady state conditions, said feed(s) are maintained such that the ratio of (i) the volume of said reaction mixture in liters to (ii) the moles of said hydantoin being fed to the reaction mixture per minute is in the range of about 30 to about 60 liters per mole per minute.

30. A process of claim 2 wherein said process is conducted in batch mode in at least one reactor and wherein, until the volume of the reaction mixture reaches 50 percent of the total volume of the reactor(s), the feeds to said reaction mixture are maintained such that the ratio of (i) the volume of said reaction mixture in liters to (ii) the moles of 5,5-dimethylhydantoin being fed to the reaction mixture per minute is in the range of about 10 to about 100 liters per mole per minute; and wherein, when the volume of the reaction mixture is 50 percent or more of the total volume of the reactor(s), the feeds to said reaction mixture are maintained such that the ratio of (i) the volume of said reaction mixture in liters to (ii) the moles of 5,5-dimethylhydantoin being fed to the reaction mixture per minute is in the range of about 30 to about 60 liters per mole per minute.

31. A process of claim 30 wherein, until the volume of the reaction mixture reaches 50 percent of the total volume of the reactor(s), the feeds to said reaction mixture are maintained such that said ratio is in the range of about 20 to about 80 liters per mole per minute.

32. A process of claim 1 wherein said inorganic base is a basic salt or oxide of an alkali metal or an alkaline earth metal; wherein the amount of such base is the stoichiometric quantity, or is substantially the stoichiometric quantity, theoretically required to deprotonate the nitrogen atoms of the 5,5dimethylhydantoin; wherein said brominating agent is (i) bromine, (ii) an alkali metal bromide or aqueous solution thereof, or an alkaline earth metal bromide or aqueous solution thereof, and chlorine, or hypochlorite salt or aqueous hypochlorite solution in amounts sufficient to generate bromine in situ, or (iii) a combination of (i) and (ii);

wherein at least all or such portion of brominating agent that is in the vapor state, if any, is fed subsurface to the liquid phase of the aqueous reaction mixture; wherein the temperature of the aqueous reaction mixture is continuously or substantially continuously maintained in the range of from about 20 to about 80° C. during all or substantially all of the time said feeding is occurring; and wherein said process is conducted in a continuous mode in which, under steady state conditions, the feeds to said reaction mixture are maintained such that the ratio of (i) the volume of said reaction mixture in liters to (ii) the moles of 5,5-dimethylhydantoin being fed to the reaction mixture per minute is in the range of about 30 to about 60 liters per mole per minute.

33. A process of claim 1 wherein said inorganic base is a basic salt or oxide of an alkali metal or an alkaline earth metal; wherein the amount of such base is the stoichiometric quantity, or is substantially the stoichiometric quantity, theoretically required to deprotonate the nitrogen atoms of the 5,5-dimethylhydantoin; wherein said brominating agent is (i) bromine, (ii) an alkali metal bromide or an alkaline earth metal bromide, and chlorine, a hypochlorite salt, or an aqueous hypochlorite solution in amounts sufficient to generate bromine in situ, or (iii) a combination of (i) and (ii); wherein at least all or such portion of said brominating agent that is in the vapor state, if any, is fed subsurface to the liquid phase of the aqueous reaction mixture; wherein the temperature of said aqueous reaction mixture is continuously or substantially continuously maintained in the range of from about 20 to about 80° C. during all or substantially all of the time said feeding is occurring; wherein said process is conducted in a batch mode in at least one reactor; wherein, until the volume of the reaction mixture reaches 50 percent of the total volume of the reactor(s), the feeds to said reaction mixture are maintained such that the ratio of (i) the volume of said reaction mixture in liters to (ii) the moles of 5,5dimethylhydantoin being fed to the reaction mixture per minute is in the range of about 20 to about 80 liters per mole per minute; and wherein, when the volume of the reaction mixture is 50 percent or more of the total volume of the reactor(s), the feeds to said reaction mixture are maintained such that the ratio of (i) the volume of said reaction mixture in liters to (ii) the moles of 5,5-dimethylhydantoin being fed to the reaction mixture per minute is in the range of about 30 to about 60 liters per mole per minute.

34. A process of claim 32 wherein said pH is in the range of about 6.8 to about 7.2.

35. A process of claim 33 wherein said pH is in the range of about 6.8 to about 7.2.

36. A process of claim 32 wherein said pH is in the range of about 6.8 to about 7.2; wherein said temperature in the range of about 30 to about 70° C.; and wherein said brominating agent is bromine.

37. A process of claim 2 wherein said pH is continuously or substantially continuously maintained in the range of about 6.8 to about 7.2 during all or substantially all of the time said feeding is occurring; wherein said temperature of the aqueous reaction mixture is maintained in the range of about 30 to about 70° C. during all or substantially all of the time said feeding is occurring; and wherein the brominating agent is bromine.

38. A process for the N-halogenation of 5,5-dimethylhydantoin, which process comprises concurrently feeding into a reaction zone, separate feeds of (i) an aqueous solution or slurry formed from an inorganic base and 5,5-dimethylhydantoin, and (ii) a brominating agent in proportions such that 1,3-dibromo-5,5-dimethylhydantoin is formed and precipitates in a liquid phase of a reaction mixture during all or substantially all of the time said concurrent feeding is occurring, and such that the pH of said mixture is continuously or substantially continuously maintained in the range of about 6.5 to about 8.5 during all or substantially all of the time said concurrent feeding is occurring.

39. A process of claim 38 wherein (ii) is bromine, and is fed subsurface to the liquid phase of the reaction mixture.

40. A process of claim 38 wherein (ii) is an alkali metal bromide or an alkaline earth metal bromide, and chlorine, a hypochlorite salt, or an aqueous hypochlorite solution in amounts sufficient to generate bromine in situ, and if (ii) is chlorine, said chlorine is fed subsurface to the liquid phase of the reaction mixture.

41. A process of claim 38 wherein the inorganic base is a water-soluble basic salt or oxide of an alkali metal or an alkaline earth metal, and wherein the amount of such base is the stoichiometric quantity, or is substantially the stoichiometric quantity, theoretically required to deprotonate the nitrogen atoms of the 5,5-dimethylhydantoin.

42. A process of claim 38 wherein said basic salt or oxide consists essentially of sodium oxide, sodium hydroxide, sodium carbonate, sodium bicarbonate, potassium oxide, potassium hydroxide, potassium carbonate, potassium bicarbonate, calcium oxide, calcium hydroxide, or a mixture of any two or more of them.

43. A process of claim 38 wherein the pH is in the range of about 6.8 to about 7.2.

44. A process of claim 38 wherein the temperature of said reaction mixture is in the range of about 0 to about 90° C., and wherein if (ii) is in the form of a vapor, (ii) is fed subsurface to the liquid phase of said reaction mixture.

45. A process of claim 38 wherein the temperature of said reaction mixture is in the range of about 30 to about 70° C., and wherein if (ii) is in the form of a vapor, (ii) is fed subsurface to the liquid phase of said reaction mixture.

46. A process of claim 38 wherein the proportions of water, inorganic base, and 5,5-dimethylhydantoin being fed are such that:
   A) where the inorganic base has a monovalent cation, there are from about 0.5 to about 2.5 moles of 5,5-dimethylhydantoin and from about 0.5 to about 2.5 moles of the base, per liter of water; and
   B) where the base has a divalent cation, there are about 0.5 to about 2.5 moles of 5,5-dimethylhydantoin and from about 0.25 to about 1.25 moles of the base, per liter of water.

47. A process of claim 38 wherein the proportions of water, inorganic base, and 5,5-dimethylhydantoin being fed are such that:
   A) where the inorganic base has a monovalent cation, there are from about 1.0 to about 1.5 moles of 5,5dimethylhydantoin and from about 1.0 to about 1.5 moles of the base, per liter of water; and
   B) where the base has a divalent cation, there are about 1.0 to about 1.5 moles of 5,5-dimethylhydantoin and from about 0.5 to about 0.75 moles of the base, per liter of water.

48. A process of claim 38 wherein the process is conducted in a batch mode in at least one reactor and wherein, until the volume of the reaction mixture reaches 50 percent of the total volume of the reactor(s), the feeds to said reaction mixture are maintained such that the ratio of (i) the volume of said reaction mixture in liters to (ii) the moles of 5,5-dimethylhydantoin being fed to the reaction mixture per minute is in the range of about 10 to about 100 liters per mole per minute; and wherein, when the volume of the reaction mixture is 50 percent or more of the total volume of the reactor(s), the feeds to said reaction mixture are maintained such that the ratio of (i) the volume of said reaction mixture in liters to (ii) the moles of 5,5dimethylhydantoin being fed to the reaction mixture per minute is in the range of about 30 to about 60 liters per mole per minute.

49. A process of claim 38 wherein the process is conducted in a continuous mode in which, under steady state conditions, said feed(s) are maintained such that the ratio of (i) the volume of said reaction mixture in liters to (ii) the moles of 5,5-dimethylhydantoin being fed to the reaction mixture per minute is in the range of about 10 to about 100 liters per mole per minute.

50. A process of claim 38 wherein when starting up said process, said feeding is initiated into a reactor containing (i) a solids-containing heel of a reaction mixture from a prior reaction in which the product to be formed had been formed, or (ii) a solids-free mother liquor of a reaction mixture from a prior reaction in which the product to be formed had been formed.

51. A process for the production of 1,3-dibromo-5,5-dimethylhydantoin, which process comprises concurrently feeding into a reaction zone (i) water, inorganic base, and 5,5-dimethylhydantoin, these being fed separately and/or in any combination(s), and (ii) a separate feed of a brominating agent in proportions such that during all or substantially all of the time the concurrent feeding is occurring 1,3-dibromo-5,5-dimethylhydantoin is formed and precipitates in the liquid phase of an aqueous reaction mixture, and in which the pH of said liquid phase is continuously or substantially continuously maintained in the range of about 6.5 to about 8.5 during all or substantially all of the time the concurrent feeding is occurring.

52. A process of claim 51 wherein said pH is in the range of about 6.8 to about 7.2.

53. A process of claim 51 wherein (ii) is bromine and is fed subsurface to the liquid phase of said reaction mixture.

54. A process of claim 51 wherein (ii) is an alkali metal bromide or an alkaline earth metal bromide, and chlorine, a hypochlorite salt, or an aqueous hypochlorite solution in amounts sufficient to generate bromine in situ, and if chlorine is used it is fed subsurface to the liquid phase of said reaction mixture.

55. A process of claim 51 wherein the temperature of said aqueous reaction mixture is in the range of about 20 to about 80° C.

56. A process of claim 51 wherein the temperature of said aqueous reaction mixture is in the range of about 30 to about 70° C.

57. A process of claim 51 wherein the temperature of said aqueous reaction mixture is in the range of about 40 to about 60° C.

58. A process of claim 51 wherein the proportions of water, inorganic base, and 5,5-dimethylhydantoin being fed are such that:
A) where the inorganic base has a monovalent cation, there are from about 0.5 to about 2.5 moles of 5,5-dimethylhydantoin and from about 1.0 to about 5.0 moles of the base, per liter of water; and
B) where the base has a divalent cation, there are about 0.5 to about 2.5 moles of 5,5-dimethylhydantoin and from about 0.5 to about 2.5 moles of the base, per liter of water.

59. A process of claim 51 wherein the proportions of water, inorganic base, and 5,5-dimethylhydantoin being fed are such that:
A) where the inorganic base has a monovalent cation, there are from about 1.0 to about 1.5 moles of 5,5-dimethylhydantoin and from about 2.0 to about 3.0 moles of the base, per liter of water; and
B) where the base has a divalent cation, there are about 1.0 to about 1.5 moles of 5,5-dimethylhydantoin and from about 1.0 to about 1.5 moles of the base, per liter of water.

60. A process of claim 59 wherein (ii) is bromine; wherein said pH is in the range of about 6.8 to about 7.2; wherein the temperature of said aqueous reaction mixture is in the range of about 30 to about 70° C.; and wherein if said temperature is above the boiling point of the bromine, the bromine is fed subsurface to the liquid phase said reaction mixture.

61. A process of claim 59 wherein (ii) is bromine; wherein said base is sodium hydroxide, wherein said pH is in the range of about 6.8 to about 7.2; wherein the temperature of said aqueous reaction mixture is in the range of about 40 to about 60° C.; wherein if said temperature is above the boiling point of the bromine, the bromine is fed subsurface to the liquid phase of said reaction mixture.

62. A process of claim 51 wherein water, inorganic base, and 5,5-dimethylhydantoin of (i) are introduced as a feed solution formed from all three of them by mixing 5,5-dimethylhydantoin with an aqueous solution of inorganic base.

63. A process of claim 62 wherein the inorganic base used in forming said feed solution is a water-soluble basic salt or oxide of an alkali metal or an alkaline earth metal; and wherein said pH is in the range of about 6.8 to about 7.2.

64. A process of claim 51 wherein the inorganic base used in forming said feed solution consists essentially of sodium oxide, sodium hydroxide, sodium carbonate, sodium bicarbonate, potassium oxide, potassium hydroxide, potassium carbonate, potassium bicarbonate, calcium oxide, calcium hydroxide, or a mixture of any two or more of them; and wherein the amount of such base is the stoichiometric quantity, or is substantially the stoichiometric quantity, theoretically required to fully deprotonate the 5,5-dimethylhydantoin used in forming said feed solution.

65. A process of claim 51 wherein the process is conducted in a batch mode by initiating the concurrent feeds of (i) and (ii) to a reactor containing (a) a solids-containing heel of a reaction mixture from a prior reaction in which the 1,3-dibromo-5,5-dimethylhydantoin to be formed had been formed, or (b) a solids-free mother liquor of a reaction mixture from a prior reaction in which the 1,3-dibromo-5,5-dimethylhydantoin to be formed had been formed, and discontinuing the concurrent feeds of (i) and (ii) when the reactor has been filled to the desired level.

66. A process of claim 62 wherein the process is conducted in a batch mode by initiating the concurrent feeds of (i) and (ii) to the reactor containing (a) a solids-containing heel of a reaction mixture from a prior reaction in which the 1,3-dibromo-5,5-dimethylhydantoin to be formed had been formed, or (b) a solids-free mother liquor of a reaction mixture from a prior reaction in which the 1,3-dibromo-5,5dimethylhydantoin to be formed had been formed, and discontinuing the concurrent feeds of (i) and (ii) when the reactor has been filled to the desired level.

67. A process of any of claims 1, 2, 14, or 38 wherein the proportions of said brominating agent and 5,5-dimethylhydantoin being fed are such that there are in the range of about 1.9 to about 2.1 atoms of bromine per nitrogen atom to be brominated.

68. A process of any of claims 51, 52, 53, 54, or 61 wherein the proportions of the brominating agent and 5,5-dimethylhydantoin being fed are such that there are in the range of about 3.8 to about 4.2 atoms of bromine per molecule of 5,5-dimethylhydantoin.

69. A process of claim 51 wherein (ii) is bromine and wherein the rate at which (i) and (ii) are being fed is such that the color of the reaction mixture is yellow to reddish yellow.

70. A process for the N-halogenation of 5,5-dimethylhydantoin which process comprises:

I) concurrently and continuously feeding into a reactor containing an aqueous reaction mixture:

A) separate feeds of (i) an aqueous solution or slurry formed from an inorganic base and 5,5-dimethylhydantoin and (ii) a brominating agent; or B) at least three separate feeds, one of which is a brominating agent, and at least two other feeds, at least one of which is selected from (a) and (b); and at least one of which is selected from (c) and (d), wherein (a) is an aqueous solution or slurry formed from an inorganic base, (b) is an aqueous solution or slurry formed from an inorganic base and 5,5-dimethylhydantoin, (c) is 5,5-dimethylhydantoin, and (d) is an aqueous solution or slurry formed from 5,5-dimethylhydantoin;

in proportions such that 1,3-dibromo-5,5-dimethylhydantoin is formed and precipitates in the liquid phase of an aqueous reaction mixture during all or substantially all of the time said concurrent feeding is occurring, and such that the pH of said reaction mixture is continuously or substantially continuously maintained in the range of about 5.5 to about 8.5 during all or substantially all of the time said concurrent feeding is occurring; and II) periodically or continuously removing precipitate and a portion of the reaction mixture from the reactor.

71. A process of claim 70 wherein the volume of the feeds to said reactor in I) and the volume of the precipitate and portion of the reaction mixture removed from said reactor in II) are equal or substantially equal so that the volume of reactor contents remains constant or substantially constant.

72. A process of claim 70 wherein said pH is in the range of about 6.5 to about 8.5.

73. A process of claim 70 wherein said pH is in the range of about 6.8 to about 7.2.

74. A process of claim 70 wherein the temperature of said aqueous reaction mixture is in the range of about 20 to about 90° C., and wherein if said brominating agent is in the form of a vapor, said vapor is fed subsurface to the liquid phase of said reaction mixture in I).

75. A process of claim 72 wherein the temperature of said aqueous reaction mixture is in the range of about 30 to about 70° C., and wherein if said brominating agent is in the form of a vapor, said vapor is fed subsurface to the liquid phase of said reaction mixture in I).

76. A process of claim 70 wherein the proportions of water, inorganic base, and 5,5dimethylhydantoin being fed are such that:

A) where the inorganic base has a monovalent cation, there are from about 0.5 to about 2.5 moles of 5,5-dimethylhydantoin and from about 0.5 to about 2.5 moles of the base, per liter of water; and B) where the base has a divalent cation, there are about 0.5 to about 2.5 moles of 5,5-dimethylhydantoin and from about 0.25 to about 1.25 moles of the base, per liter of water.

77. A process of claim 70 wherein the proportions of water, inorganic base, and 5,5-dimethylhydantoin being fed are such that:

A) where the inorganic base has a monovalent cation, there are from about 1.0 to about 1.5 moles of 5,5-dimethylhydantoin and from about 1.0 to about 1.5 moles of the base, per liter of water; and B) where the base has a divalent cation, there are about 1.0 to about 1.5 moles of 5,5-dimethylhydantoin and from about 0.5 to about 0.75 moles of the base, per liter of water.

78. A process of claim 70 wherein said brominating agent is bromine, and is fed subsurface to the liquid phase of the reaction mixture in I).

79. A process of claim 70 wherein said brominating agent is an alkali metal bromide or an alkaline earth metal bromide and chlorine, a hypochlorite salt, or an aqueous hypochlorite solution in amounts sufficient to generate bromine in situ, and if chlorine is used, said chlorine is fed subsurface to the liquid phase of the aqueous reaction mixture in I).

80. A process of any of claims 76 or 77 wherein said brominating agent is bromine, and wherein the bromine is fed subsurface to the liquid phase of the aqueous reaction mixture in I).

81. A process of claim 70 wherein the bromine is fed as a mixture of bromine vapor and at least one inert gas.

82. A process of claim 70 wherein said inorganic base and 5,5-dimethylhydantoin are fed either as separate solutions or slurries in water or as a single solution or slurry in water.

83. A process of claim 82 wherein the inorganic base used in forming the solution, solutions, slurry, and/or slurries is a water-soluble basic salt or oxide of an alkali metal or an alkaline earth metal.

84. A process of claim 82 wherein the inorganic base used in forming the solution, solutions, slurry, and/or slurries consists essentially of sodium oxide, sodium hydroxide, sodium carbonate, sodium bicarbonate, potassium oxide, potassium hydroxide, potassium carbonate, potassium bicarbonate, calcium oxide, calcium hydroxide, or a mixture of any two or more of them.

85. A process of claim 76 wherein said pH is in the range of about 6.8 to about 7.2; wherein the temperature of said aqueous reaction mixture is in the range of about 30 to about 90° C.; wherein if said brominating agent is in the form of a vapor, said vapor is fed subsurface to the liquid phase of the reaction mixture in I); and wherein said inorganic base and 5,5-dimethylhydantoin are fed either as separate solutions or slurries in water or as a single solution or slurry in water.

86. A process of claim 85 wherein the inorganic base used in forming said solution or slurry is a water-soluble basic salt or oxide of an alkali metal or an alkaline earth metal; wherein said brominating agent is bromine; and wherein the bromine is fed subsurface to the liquid phase of the aqueous reaction mixture in I).

87. A process of claim 86 wherein the bromine is fed as a mixture of bromine vapor and at least one inert gas.

88. A process of claim 77 wherein said pH is in the range of about 6.8 to about 7.2; wherein the temperature of said aqueous reaction mixture is in the range of about 30 to about 70° C.; wherein if all or a portion of said brominating agent is in the form of a vapor, at least said vapor is fed subsurface to the liquid phase of said reaction mixture in I); and wherein said inorganic base and 5,5-dimethylhydantoin are fed either as separate solutions or slurries in water or as a single solution or slurry in water.

89. A process of claim 88 wherein the inorganic base used is a water-soluble basic salt or oxide of an alkali metal or an alkaline earth metal; wherein said brominating agent is bromine; and wherein the bromine is fed subsurface to the liquid phase of the aqueous reaction mixture in I).

90. A process of claim 89 wherein the bromine is fed as a mixture of bromine vapor and at least one inert gas.

91. A process of claim 70 wherein said pH is in the range of about 6.8 to about 7.2.

92. A process of claim 91 wherein the temperature of said aqueous reaction mixture is in the range of about 20 to about

37

80° C., and wherein if all or a portion of said brominating agent is in the form of a vapor, at least said vapor is fed subsurface to the liquid phase of said reaction mixture in I).

93. A process of claim 92 wherein said temperature is in the range of about 40 to about 60° C.

94. A process of claim 91 wherein the proportions of water, inorganic base, and 5,5-dimethylhydantoin being fed are such that:
   A) where the inorganic base has a monovalent cation, there are from about 0.5 to about 2.5 moles of 5,5-dimethylhydantoin, and from about 1.0 to about 5.0 moles of the base, per liter of water; and
   B) where the base has a divalent cation, there are about 0.5 to about 2.5 moles of 5,5-dimethylhydantoin, and from about 0.5 to about 2.5 moles of the base, per liter of water.

95. A process of claim 91 wherein the proportions of water, inorganic base, and 5,5-dimethylhydantoin being fed are such that:
   A) where the inorganic base has a monovalent cation, there are from about 1.0 to about 1.5 moles of 5,5-dimethylhydantoin and from about 2.0 to about 3.0 moles of the base, per liter of water, and
   B) where the base has a divalent cation, there are about 1.0 to about 1.5 moles of 5,5-dimethylhydantoin and from about 1.0 to about 1.5 moles of the base, per liter of water.

96. A process of claim 91 wherein said brominating agent is bromine, and is fed subsurface to the liquid phase of the aqueous reaction mixture in I).

97. A process of claim 91 wherein said brominating agent is an alkali metal bromide or an alkaline earth metal bromide and chlorine, hypochlorite salt, or an aqueous hypochlorite solution in amounts sufficient to generate bromine in situ, and wherein if chlorine is used, said chlorine is fed subsurface to the aqueous reaction mixture in I).

98. A process of claim 91 wherein said brominating agent is bromine, and wherein the bromine is fed subsurface to the aqueous reaction mixture in I).

99. A process of claim 98 wherein the bromine is fed as a mixture of bromine vapor and at least one inert gas.

100. A process of claim to 91 wherein said inorganic base and said 5,5-dimethylhydantoin are fed either as separate solutions or slurries or as a single solution or slurry in water.

101. A process of claim 100 wherein the inorganic base used in forming the solution, solutions, slurry and/or slurries is a water-soluble basic salt or oxide of an alkali metal or an alkaline earth metal.

102. A process of claim 91 wherein the inorganic base used in forming the solution, solutions, slurry, and/or slurries consists essentially of sodium oxide, sodium hydroxide, sodium carbonate, sodium bicarbonate, potassium oxide, potassium hydroxide, potassium carbonate, potassium bicarbonate, calcium oxide, calcium hydroxide, or a mixture of any two or more of them.

103. A process of claim 100 wherein the temperature of said aqueous reaction mixture is in the range of about 40 to about 60° C.; wherein if all or a portion of said brominating agent is in the form of a vapor, at least said vapor is fed subsurface to the liquid phase of the aqueous reaction mixture in I); and wherein the proportions of water, inorganic base, and 5,5-dimethylhydantoin being fed are such that:
   A) where the inorganic base has a monovalent cation, there are from about 0.5 to about 2.5 moles of 5,5-dimethylhydantoin and from about 1.0 to about 5.0 moles of the base, per liter of water; and
   B) where the base has a divalent cation, there are about 0.5 to about 2.5 moles of 5,5-dimethylhydantoin and from about 0.5 to about 2.5 moles of the base, per liter of water.

38

104. A process of claim 103 wherein said brominating agent is bromine; and wherein the bromine is fed subsurface to the liquid phase of the aqueous reaction mixture in I).

105. A process of claim 104 wherein the bromine is fed as a mixture of bromine vapor and at least one inert gas.

106. A process of claim 103 wherein the proportions of water, inorganic base, and 5,5dimethylhydantoin being fed are such that:
   A) where the inorganic base has a monovalent cation, there are from about 1.0 to about 1.5 moles of 5,5dimethylhydantoin and from about 2.0 to about 3.0 moles of the base, per liter of water; and
   B) where the base has a divalent cation, there are about 1.0 to about 1.5 moles of 5,5-dimethylhydantoin and from about 1.0 to about 1.5 moles of the base, per liter of water.

107. A process of claim 106 wherein said brominating agent is bromine; and wherein the bromine is fed subsurface to the liquid phase of the aqueous reaction mixture in I).

108. A process of claim 107 wherein the bromine is fed as a mixture of bromine vapor and at least one inert gas.

109. A process of claim 2 or 70 wherein the process is conducted adiabatically and with agitation of the aqueous reaction mixture.

110. A process of claim 91 wherein the halogen is bromine and wherein the rate at which the feeds are being fed is such that the color of the reaction mixture is yellow to reddish yellow.

111. A process of any of claims 70, 85, or 88 wherein the proportions of said brominating agent and 5,5-dimethylhydantoin being fed are such that there are in the range of about 3.8 to about 4.2 atoms of bromine per atom of nitrogen.

112. A process of any of claims 91, 92, 96, 97, 100, 103, 106, or 117 wherein the proportions of halogen and 5,5-dimethylhydantoin being fed are such that there are in the range of about 3.8 to about 4.2 atoms of halogen per molecule of 5,5-dimethylhydantoin.

113. A process for the N-halogenation of 5,5-dimethylhydantoin, which process comprises:
   a) concurrently feeding into a reactor (i) water, inorganic base, and 5,5-dimethylhydantoin, these components being fed separately and/or in any combination(s), and (ii) a separate feed of a brominating agent, in proportions such that:
      1) both nitrogen atoms of the 5,5dimethylhydantoin become substituted by a bromine atom;
      2) during all or substantially all of the time the concurrent feeding is occurring, the product precipitates in the liquid phase of an aqueous reaction mixture in which the pH is continuously or substantially continuously maintained in the range of about 5.5 to about 8.5; and
      3), an aqueous solution of co-product inorganic bromide salt is formed;
   b) separating precipitate from said aqueous solution; and
   c) oxidizing co-product inorganic bromide salt in said solution to form elemental bromine.

114. A process of claim 113 wherein said oxidation is accomplished using chlorine.

115. A process of claim 113 wherein said pH is in the range of about 6.5 to about 8.5.

116. A process of any of claims 113–115 wherein said inorganic base is a water-soluble basic salt or oxide of an alkali metal or an alkaline earth metal; and wherein said brominating agent is bromine fed subsurface to the liquid phase of the aqueous reaction mixture.

117. A process of claim 113 wherein said pH is maintained in the range of about 6.8 to about 7.2; and wherein the temperature of said reaction mixture is maintained in the range of about 40 to about 60° C.

118. A process of claim 113 wherein in a) the feeds are being fed such that the color of the aqueous reaction mixture is yellow to reddish yellow.

119. A process of any of claims 2, 38, or 51 wherein an aqueous solution of co-product inorganic bromide salt is formed; wherein precipitate is separated from said aqueous solution; and wherein co-product inorganic bromide salt in said solution is oxidized to form elemental bromine.

120. A process of claim 70 wherein co-product inorganic bromide salt is formed in the aqueous reaction mixture; wherein the inorganic bromide salt in the aqueous solution remaining after said precipitate has been removed therefrom is oxidized to form elemental bromine.

* * * * *